(12) United States Patent
Zhang et al.

(10) Patent No.: US 11,852,754 B2
(45) Date of Patent: Dec. 26, 2023

(54) ULTRAFAST ULTRASOUND IMAGING WITH CASCADED DUAL-POLARITY WAVES

(71) Applicant: VERSITECH LIMITED, Hong Kong (CN)

(72) Inventors: Yang Zhang, Hong Kong (CN); Yuexin Guo, Hong Kong (CN); Wei-Ning Lee, Hong Kong (CN)

(73) Assignee: Versitech Limited, Hong Kong (CN)

(*) Notice: Subject to any disclaimer, the term of this patent is extended or adjusted under 35 U.S.C. 154(b) by 0 days.

(21) Appl. No.: 16/767,009

(22) PCT Filed: Dec. 5, 2018

(86) PCT No.: PCT/CN2018/119321
§ 371 (c)(1),
(2) Date: May 26, 2020

(87) PCT Pub. No.: WO2019/114585
PCT Pub. Date: Jun. 20, 2019

(65) Prior Publication Data
US 2021/0000450 A1    Jan. 7, 2021

Related U.S. Application Data

(60) Provisional application No. 62/597,708, filed on Dec. 12, 2017.

(51) Int. Cl.
*A61B 8/14* (2006.01)
*G01S 7/52* (2006.01)
*G01S 15/89* (2006.01)

(52) U.S. Cl.
CPC .......... *G01S 7/52026* (2013.01); *A61B 8/14* (2013.01); *G01S 15/8927* (2013.01); *G01S 15/8959* (2013.01)

(58) Field of Classification Search
CPC ......... A61B 8/5269; A61B 8/00; A61B 8/483; A61B 8/14; A61B 5/0507; A61B 8/485;
(Continued)

(56) References Cited

U.S. PATENT DOCUMENTS 5,148,810 A  *  9/1992  Maslak ............... G01S 15/8927
                                                          600/447
6,048,315 A  *  4/2000  Chiao ................. G01S 15/8997
                                                          600/447
(Continued)

FOREIGN PATENT DOCUMENTS

CN        104546003 A    4/2015
WO    WO-2017/055435 A1  4/2017

OTHER PUBLICATIONS

Demene et al., "Spatiotemporal Clutter Filtering of Ultrafast Ultrasound Data Highly Increases Doppler and fUltrasound Sensitivity", Nov. 2015, IEEE Transactions on Medical Imaging, vol. 34 No. 11, pp. 2271-2285 (Year: 2015).*

(Continued)

*Primary Examiner* — Patricia J Park
*Assistant Examiner* — Adil Partap S Virk
(74) *Attorney, Agent, or Firm* — Saliwanchik, Lloyd & Eisenschenk

(57) ABSTRACT

System and method of ultrasound imaging methodology are provided. The system and method can include directing an array to transmit sets of cascaded titled ultrasound waves towards a tissue sample, decoding reflected signals through summing, subtracting, and delay operations. The reflected signals can be reconstructed to provide a final decoded output.

9 Claims, 17 Drawing Sheets

(58) Field of Classification Search
CPC ..... A61B 8/488; A61B 8/5207; A61B 8/4488; G01S 7/5202; G01S 15/8927; G01S 15/895; G01S 15/8959; G01S 15/8995; G01S 15/8997

See application file for complete search history.

(56) References Cited

U.S. PATENT DOCUMENTS

| | | | |
|---|---|---|---|
| 2005/0131295 A1* | 6/2005 | Li | A61B 8/483 600/443 |
| 2006/0241429 A1* | 10/2006 | Ustuner | G01S 7/52046 600/437 |
| 2015/0141832 A1* | 5/2015 | Yu | G06T 7/20 600/455 |
| 2015/0320395 A1* | 11/2015 | Sato | A61B 8/06 600/455 |
| 2015/0359521 A1* | 12/2015 | Santos | A61B 8/54 600/447 |
| 2016/0213258 A1* | 7/2016 | Lashkari | G01S 15/8915 |
| 2019/0261948 A1* | 8/2019 | Gong | G01S 7/5202 |
| 2020/0041644 A1* | 2/2020 | Brown | G01S 15/8993 |
| 2020/0183004 A1* | 6/2020 | Gong | G01S 15/8977 |

OTHER PUBLICATIONS

Synnevag et al., "Adaptive Beamforming Applied to Medical Ultrasound Imaging", Aug. 2007, IEEE Transactions on Ultrasonics, Ferroelectrics, and Frequency Control, vol. 54 No. 8, pp. 1606-1613 (Year: 2007).*

Mikla et al., "Medical Imaging Technology", 2014 (Year: 2014).*

Gong et al. "Hadamard-Encoded Multipulses for Contrast-Enhanced Ultrasound Imaging", Nov. 2017, vol. 64, No. 11 (Year: 2017).*

Misaridis et al. "Space-time encoding for high frame rate ultrasound imaging", 2002 (Year: 2002).*

Karaman et al., "Synthetic Aperture Imaging for Small Scale Systems", May 1995, IEEE Transactions On Ultrasonics, Ferroelectrics, and Frequency Control, vol. 42, No. 3 (Year: 1995).*

Chiao et al., "Synthetic Transmit Aperture Imaging Using Orthogonal Golay Coded Excitation", 2000, IEEE Ultrasonics Symposium (Year: 2000).*

Misaridis et al., "Space-time encoding for high frame rate ultrasound imaging", 2002, Ultrasonics 40 (2002) 593-597 (Year: 2002).*

Gong et al., "Delay-Encoded Transmission and Image Reconstruction Method in Synthetic Transmit Aperture Imaging", Oct. 2015, IEEE Transactions On Ultrasonics, Ferroelectrics, and Frequency Control, vol. 62, No. 10 (Year: 2015).*

Zhang, Y. et al., "Ultrafast Ultrasound Imaging With Cascaded Dual-Polarity Waves", IEEE Transactions on Medical Imaging, Apr. 2018, 37(4):906-917, IEEE.

Zhang, Y. et al., "Ultrafast Ultrasound Imaging Using Combined Transmissions With Cross-Coherence-Based Reconstruction", IEEE Transactions on Medical Imaging, Feb. 2018, 37(2):337-348, IEEE.

International Search Report and Written Opinion dated Feb. 27, 2019 issued in International Application No. PCT/CN2018/119321.

* cited by examiner

A: Left part of the first row, B: Right part of the first row;
C: Left part of the second row, D: Right part of the second row.

$C_{2\times N} = \left[\begin{array}{c|c} C_{11} & C_{12} \\ \hline C_{21} & C_{22} \end{array}\right]$ $C_{11}$: Left part of the first row;
$C_{12}$: Right part of the first row;
$C_{21}$: Left part of the second row;
$C_{22}$: Right part of the second row.

$H_{2\times 2} = \begin{bmatrix} H_1 \\ H_2 \end{bmatrix} = \begin{bmatrix} +1 & +1 \\ +1 & -1 \end{bmatrix}$ $\Longrightarrow$ $C_N H_2 = \begin{bmatrix} H_1^T \cdot C_{11} & H_2^T \cdot C_{12} \\ H_1^T \cdot C_{21} & H_2^T \cdot C_{22} \end{bmatrix}$ $H_{4\times 4} = \begin{bmatrix} H_1 \\ H_2 \\ H_3 \\ H_4 \end{bmatrix} = \begin{bmatrix} +1 & +1 & +1 & +1 \\ +1 & -1 & +1 & -1 \\ +1 & +1 & -1 & -1 \\ +1 & -1 & -1 & +1 \end{bmatrix}$ $\Longrightarrow$ $C_N H_4 = \begin{bmatrix} H_1^T \cdot C_{11} & H_2^T \cdot C_{12} \\ H_1^T \cdot C_{21} & H_2^T \cdot C_{22} \\ H_3^T \cdot C_{11} & H_4^T \cdot C_{12} \\ H_3^T \cdot C_{21} & H_4^T \cdot C_{22} \end{bmatrix}$ $H_{M\times M} = \begin{bmatrix} H_1 \\ H_2 \\ \vdots \\ H_M \end{bmatrix} = \begin{bmatrix} +1 & \cdots & +1 \\ \vdots & \ddots & \vdots \\ +1 & \cdots & +1 \end{bmatrix}$ $\Longrightarrow$ $C_N H_M = \begin{bmatrix} H_1^T \cdot C_{11} & H_2^T \cdot C_{12} \\ H_1^T \cdot C_{21} & H_2^T \cdot C_{22} \\ H_3^T \cdot C_{11} & H_4^T \cdot C_{12} \\ H_3^T \cdot C_{21} & H_4^T \cdot C_{22} \\ \vdots & \vdots \\ H_{M-1}^T \cdot C_{11} & H_M^T \cdot C_{12} \\ H_{M-1}^T \cdot C_{21} & H_M^T \cdot C_{22} \end{bmatrix}$

Fig. 13

T1-R1, T2-R2, T3-R3, and T4-R4 indicate the 1st, 2nd, 3rd, and 4th transmission-reception events.

ULTRAFAST ULTRASOUND IMAGING WITH CASCADED DUAL-POLARITY WAVES

CROSS-REFERENCE TO RELATED APPLICATIONS

This application is the U.S. national stage application of International Patent Application No. PCT/CN2018/119321, filed Dec. 5, 2018, which claims the benefit of U.S. Provisional Application No. 62/597,708, filed Dec. 12, 2017, the disclosure of each of which is incorporated herein by reference in its entirety.

TECHNICAL FIELD

The present disclosure relates to the ultrafast imaging with cascaded dual-polarity waves.

BACKGROUND

Ultrafast imaging using plane waves or diverging waves, instead of the focused beams, is a paradigm shift for biomedical ultrasound imaging from real-time acquisitions (tens of frames per second) to the ultrafast category (thousands of frames per second). It emboldens the development of novel ultrasound imaging methods for evaluating tissue functions beyond anatomical information, such as the shear wave elastography, ultrafast Doppler imaging, contrast agent dynamics, myocardial strain imaging, and parametric imaging.

Originally, the ultrafast imaging system was based on a flat plane-wave transmission. An ultrafast imaging system was developed with a flat plane-wave illumination and parallel beamforming techniques to track a low-frequency (200 Hz) transient shear wave propagation through the gel-based phantoms. A plane-wave transmission with limited diffraction beam reception was proposed to reconstruct two-dimensional (2D) and three-dimensional (3D) images in the Fourier domain with a frame rate up to 3,750 fps for biological tissues at a depth of 200 mm. The frame rate of the flat plane-wave-based imaging can reach the physical limits of medical ultrasound imaging, but the image quality in terms of resolution, contrast, and the signal-to-noise ratio (SNR) was much more degraded than the conventional focused imaging because of the lack of transmit focus.

Thereafter, coherent plane-wave compounding (CPWC), which exploited a coherent recombination of tilted plane-wave transmissions, was proposed to obtain images with equivalent spatial resolution, contrast, and SNR to conventional multi-focus imaging while preserving the high frame-rate capabilities. Similarly, coherent compounding of full aperture diverging waves and sub-aperture diverging waves (CDWC) were further developed for high frame-rate cardiac imaging. A tradeoff between the image quality and the frame rate for the coherent compounding techniques was balanced by the flexible selection of the compounded tilted plane waves or diverging waves. For example, two to five waves are typically used for transient shear wave elastography to ensure a frame rate more than 1 kHz because the typical spectrum of interest of shear waves propagating in the human body is between 100 to 500 Hz. At such a high frame rate, image contrast and SNR are compromised, and the use of plane wave transmissions leads to the known inherent axial lobe artifact.

Both the frame rate and SNR are valuable for medical ultrasound imaging. Higher SNR enables deep tissue imaging and increases the sensitivity and accuracy for mapping tissue functions beyond anatomical information. In addition, higher SNR also enables the use of higher frequencies, together yielding images with better resolution and contrast. Due to the safety issues of the medical ultrasound imaging, the maximum allowable Mechanical Index (MI) limits the maximum amplitude of the transmitted signals. Therefore, methods to increase the SNR without changing the amplitude of the transmitted signals need to be investigated. Conventional coded excitation techniques, such as chirp and Golay code, could increase the SNR of medical ultrasound imaging. For the chirp and Golay excitations, long modulated signals, instead of a short pulse, are transmitted, and the received signals are decoded by the correspondingly designed pulse compression filter. However, the decoding of chirp signals requires a priori knowledge of the signal propagation properties of the medium, such as the attenuation, to design the pulse compression filter. The application of Golay code in ultrasound imaging leads to a reduction of the frame rate by a factor of 2; which is not desirable in ultrafast imaging. Recently, a multiplane wave (MW) imaging method using Hadamard encoding was proposed to increase the SNR of ultrafast imaging without compromising the frame rate. Unlike the conventional coded excitation techniques, by which long modulated signals are transmitted and the received signals are decoded by the designed pulse compression filter, MW imaging transmits successively multiple tilted plane waves encoded by a Hadamard matrix with the short time interval for each transmission-acquisition event. The high-intensity signals from each tilted plane-wave transmission can be decoded from the received signals in different transmission-acquisition events. The decoding process relies on addition and subtraction operations without a cumbersome pulse compression filter design. MW improves the SNR by $10 \cdot \log_{10}(M)$ when M steering angles and acquisitions are used. MW imaging has been demonstrated to yield accurate elasticity maps with a smaller variance for shear wave elastography and detect deeper blood signals in ultrafast Doppler imaging compared with CPWC. MW imaging has further been combined with the delay-encoded harmonic imaging to improve both the SNR and resolution of ultrafast images. Nonetheless, SNR improvement is limited to the number of compounded tilted plane waves or diverging waves. For example, the improvement of SNR is only 3 dB for shear wave elastography with two compounded tilted plane waves to ensure the ultrafast frame rates. In addition, the number of compounded tilted plane waves is bound to $M=2^m$, where m is an integer. A remaining challenge to tackle is greater SNR improvement in ultrafast imaging with as few compounded transmissions as possible.

Further, pulsed-wave ultrasound (PUS), instead of cascaded-wave ultrasound (CUS), is conventionally used in the high frame-rate or ultrafast paradigm to trade the length of the transmitted ultrasound signals (i.e., acoustic intensity) for spatial resolution. Conventional ultrafast PUS can be achieved in either focused or unfocused wave transmission modes. One example in the category of focused PUS is multiline transmit imaging. Multiple focused beams are transmitted simultaneously to increase the frame rate, but the cross-talk between the transmitted beams likely causes image artifacts. In the case of unfocused PUS, synthetic aperture (SA) imaging is widely accepted, where a diverging wave is transmitted by a single element or a virtual-source-based sub-aperture to obtain one low-quality image with a large field-of-view (FOV). Multiple low-quality images yielded from different elements or sub-apertures are coherently summed to obtain a high-quality image. Since the SA uses single element or sub-aperture in each transmission, its SNR is lower than that of the full-aperture transmission. In order to further increase the SNR, a Hadamard encoded synthetic aperture (H-SA) imaging is proposed to fully utilize the spatial domain of the array elements. Unlike SA imaging, which only activates partial array elements in each transmission, H-SA utilizes full aperture in the transmission event with Hadamard coefficients applied to each element or sub-aperture. In reception, a decoding process is realized to increase SNR without compromising other primary image characteristics, such as spatial resolution. Even though aforementioned PUS-based ultrafast imaging methods fully utilize the spatial-domain of the array, their sonographic SNR and penetration remain limited. It is mainly because of the insufficient energy delivery by the short ultrasound pulses (microseconds) and attenuated ultrasound waves through the chest wall to reach the heart. Thus, there is a need to solve the tradeoff between the length of transmitted ultrasound signals and spatial resolution while achieving ultrafast frame rates.

BRIEF SUMMARY

Embodiments of the subject invention provide systems and methods for ultrasound imaging using a coding matrix whose length is longer than the square Hadamard matrix of order 2. The ultrafast ultrasound imaging method herein is hereinafter described as "Cascaded Dual-polarity Waves (CDW) Imaging" for increasing SNR and sensitivity in ultrafast imaging with few compounded transmissions.

Embodiments of the subject invention provide an ultrafast ultrasound imaging methodology with CDW, which comprises a pulse train with positive and negative polarities. Embodiments of the subject invention provide a coding scheme and a corresponding linear decoding process that can obtain high intensity backscattered signals, thus increasing SNR without compromising the frame rate.

Embodiments of the subject invention provide a 2×N matrix with two polarities: +1 and −1, and N=$2^k$, where k is an integer. Based on the CDW code, N cascaded dual-polarity waves can be transmitted for each reception, unlike one single wave in conventional CPWC. The corresponding decoding process comprises of addition, subtraction, and delay operations. The process can produce gains of a sonographic SNR of $10 \cdot \log_{10}(N)$. In addition to ultrasound imaging, the CDW imaging has a potential to improve the SNR of other array-based imaging modalities, such as microwave imaging.

Embodiments of the subject invention further provide systems and methods for ultrasound imaging using a matrix of sub-aperture divergent CDW with short time intervals and +1 or −1 polarity coefficients, which is described as "Cascaded Synthetic Aperture Imaging (CaSA)".

Embodiments of the subject invention further provide a method for ultrasound imaging, the method comprising transmitting an incident signal towards an object of interest; receiving sets of reflected signals from the object of interest; and decoding the reflected signals to recover an output, wherein the incident signal is an array comprised of sets of N number of titled cascaded waves and M number of sub-apertures, wherein N=$2^k$ and k is an integer, wherein M=$2^q$ and q is an integer, wherein the waves of the incident signal have predetermined polarities.

Embodiments of the subject invention further provide an ultrasound imaging system, the system comprising a transmitter configured to transmit an incident signal towards an object of interest; a receiver configured to receive sets of reflected signals from the object of interest; and a processor configured to decode the reflected signals to recover an output, wherein the incident signal is an array comprised of sets of N number of titled cascaded waves and M number of sub-apertures, wherein N=$2^k$ and k is an integer, wherein M=$2^q$ and q is an integer, wherein the waves of the incident signal have predetermined polarities.

BRIEF DESCRIPTION OF THE DRAWINGS

FIG. 13 shows a design of the spatiotemporal coding matrix $C_N H_M$.

FIG. 16 (b) shows an example of B-mode image of a calibration phantom by H-SA method; FIG. 16 (c) shows an example of B-mode image of a calibration phantom by CaSA method, wherein FIGS. 16(a)-(c) show the point target regions and the cyst regions. FIG. 16 (d) shows a plot of the axial profiles along the strong reflectors around azimuth 20 mm from the examples as shown in FIGS. 16 (a)-(c); and FIG. 16 (e) shows a plot of the gain in SNR of H-SA and CaSA compared with that of SA around azimuth 10 mm from the examples as shown in FIGS. 16 (a)-(c).

FIG. 17 (d) shows a plot of the axial profile at azimuth 29 mm from the examples as shown in FIGS. 17 (a)-(c); and FIG. 17 (e) shows a plot of the lateral profile at depth 78 mm from the examples as shown in FIGS. 17 (a)-(c).

FIGS. 18 (e)-(g) show examples of the displacement maps of the myocardium in the apical four-chamber view based on respective SA, H-SA and CaSA reconstructed images at a systolic phase; FIG. 18 (d) shows a plot of the temporal profile of displacement SNR in the septum during diastole; and FIG. 18 (h) shows a plot of the displacement SNR in the septum region during systole.

FIG. 19 (d) is a plot of the axial profile at azimuth −12 mm from the examples as shown in FIGS. 19 (a)-(c); and FIG. 19 (e) is a plot of the lateral profile at depth 55 mm from the examples as shown in FIGS. 19 (a)-(c).

DETAILED DESCRIPTION

Embodiments of the subject invention provide a cascaded dual-polarity waves (CDW) scheme to further elevate the SNR of received signals. Although a Hadamard matrix can increase the SNR of the recovered received signals, the improvement is limited to the order of the matrix (i.e. only two times for each pair of transmissions). A CDW coding and decoding scheme makes use of cascaded wave transmissions to profoundly improve the SNR of the recovered received signals. In the CDW scheme, each transmitted signal can contain N ($N=2^k$, k=0, 1, 2, . . . ) waves to gain SNR of $10 \cdot \log_{10}(N)$ on the energy. The signals for each pair of the successive transmissions are given by:

$$\begin{cases} x_{s1}(t) = \sum_{i=1}^{2^{k-1}} a_{1i} \cdot s_1(t) * \delta(t-(i-1) \cdot \tau) + \\ \qquad \sum_{i=2^{k-1}+1}^{N} a_{1i} \cdot s_2(t) * \delta(t-(i-1) \cdot \tau) \\ x_{s2}(t) = \sum_{i=1}^{2^{k-1}} a_{2i} \cdot s_1(t) * \delta(t-(i-1) \cdot \tau) + \\ \qquad \sum_{i=2^{k-1}+1}^{N} a_{2i} \cdot s_2(t) * \delta(t-(i-1) \cdot \tau) \end{cases} \quad (1)$$

Each set of N waves can contain at least two source signals, (for example, $s_1(t)$ and $s_2(t)$, in the above referenced expression), with preset delays, and different polarities or phase coefficients, which can be determined by the CDW coding matrix.

Figure 1:
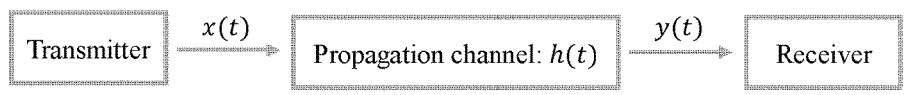
FIG. 1 shows a block diagram of a transmitter and receiver model.
Figure 2:
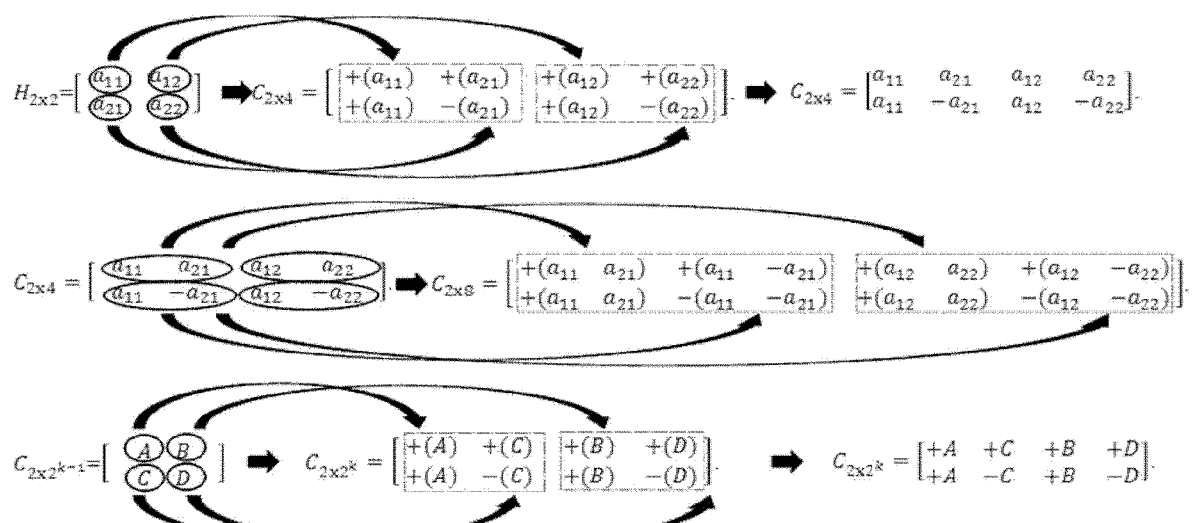
FIG. 2 shows an illustration of a design of the CDW coding matrix according to an embodiment of the subject invention.

FIG. 2 illustrates a four-wave (N=4) model. For N=2, the CDW coding matrix can be the same as the Hadamard matrix of order 2 ($H_{2\times 2}$), from which the 2×4 CDW matrix can be designed in following steps:

1) A 2-by-4 matrix can first written by repeating $H_{2\times}$:

$$C'_{2\times 4} = [H_{2\times 2} \quad H_{2\times 2}] = \begin{bmatrix} +1 & +1 & +1 & +1 \\ +1 & -1 & +1 & -1 \end{bmatrix} \quad (2)$$

where the third and the fourth columns are simply a duplicate of the first and second columns of $H_{2\times 2}$, respectively. This step sets the default sign of $C''_{2\times 4}$.

2) Another 2-by-4 matrix can be created by taking each element from $H_{2\times 2}$; and its replica to form a column vector and then concatenating the four column vectors:

$$C''_{2\times 4} = \begin{bmatrix} a_{11} & a_{21} & a_{12} & a_{22} \\ a_{11} & a_{21} & a_{12} & a_{22} \end{bmatrix} \quad (3)$$

3) The final 2-by-4 CDW matrix can be obtained by the element-wise multiplication of $C'_{2\times 4}$ and $C''_{2\times 4}$, as:

$$C_{2\times 4} = C'_{2\times 4} .* C''_{2\times 4} = \begin{bmatrix} a_{11} & a_{21} & a_{12} & a_{22} \\ a_{11} & -a_{21} & a_{12} & -a_{22} \end{bmatrix} = \begin{bmatrix} 1 & 1 & 1 & -1 \\ 1 & -1 & 1 & 1 \end{bmatrix} \quad (4)$$

where $a_{11}=a_{12}=a_{21}=1$, $a_{22}=-1$, and denotes the element-by-element multiplication of the two matrices. The first and second rows in $C_{2\times 4}$ represent the first and second transmissions, respectively. Each transmission is comprised of four waves.

Signals for each pair of successive transmissions with four waves can therefore be formulated as:

$$\begin{cases} x_{s1}(t) = s_1(t) + s_1(t) * \delta(t-\tau) + \\ \quad s_2(t) * \delta(t-2\tau) - s_2(t) * \delta(t-3\tau) \\ x_{s2}(t) = s_1(t) - s_1(t) * \delta(t-\tau) + \\ \quad s_2(t) * \delta(t-2\tau) + s_2(t) * \delta(t-3\tau) \end{cases} \quad (5)$$

Then, the received signals can be expressed as follows:

$$\begin{cases} y_{s1}(t) = s_1(t)*h(t) + s_1(t)*\delta(t-\tau)*h(t) + \\ \qquad s_2(t)*\delta(t-2\tau)*h(t) - s_2(t)*\delta(t-3\tau)*h(t) \\ y_{s2}(t) = s_1(t)*h(t) - s_1(t)*\delta(t-\tau)*h(t) + \\ \qquad s_2(t)*\delta(t-2\tau)*h(t) + s_2(t)*\delta(t-3\tau)*h(t) \end{cases} \quad (6)$$

Following the reception of backscattered signals, a linear decoding process designed based on addition, subtraction and delay operations can be as follows:

1) The received signals from the paired transmissions are summed and subtracted to obtain:

$$\begin{cases} y'_{s1}(t) = y_{s1}(t) + y_{s2}(t) = \\ \qquad 2 \cdot s_1(t)*h(t) + 2 \cdot s_2(t)*\delta(t-2\tau)*h(t) \\ y'_{s2}(t) = y_{s1}(t) - y_{s2}(t) = \\ \qquad 2 \cdot s_1(t)*\delta(t-\tau)*h(t) - 2 \cdot s_2(t)*\delta(t-3\tau)*h(t) \end{cases} \quad (7)$$

2) $y'_{s2}(t)$ can be compensated by the delay operation to obtain:

$$y''_{s2}(t) = y'_{s2}(t)*\delta(t+\tau) = 2 \cdot s_1(t)*h(t) - 2 \cdot s_2(t)*\delta(t-2\tau)*h(t) \quad (8)$$

3) $y'_{s1}(t)$ and $y''_{s2}(t)$ can be summed or subtracted to obtain:

$$\begin{cases} y''_{s1}(t) = y'_{s1}(t) + y''_{s2}(t) = 4 \cdot s_1(t)*h(t) \\ y'''_{s2}(t) = y'_{s1}(t) - y''_{s2}(t) = 4 \cdot s_2(t)*\delta(t-2\tau)*h(t) \end{cases} \quad (9)$$

4) $y'''_{s2}(t)$ can similarly be compensated by the delay operation to obtain:

$$y''''_{s2}(t) = y'''_{s2}(t)*\delta(t+2\tau) = 4 \cdot s_2(t)*h(t). \quad (10)$$

5) The final decoded signals with high amplitude can be expressed as follows:

$$\begin{cases} y''_{s1}(t) = 4 \cdot s_1(t)*h(t) = 4 \cdot y_1(t) \\ y''''_{s2}(t) = 4 \cdot s_2(t)*h(t) = 4 \cdot y_2(t) \end{cases} \quad (11)$$

Similar to the $C_{2\times4}$ CDW matrix derived from the $H_{2\times2}$ Hadamard matrix, the $C_{2\times8}$ CDW matrix can be obtained with the described coding procedure from the $C_{2\times4}$ CDW matrix as shown in FIG. 2. The difference is that the elements in the first and the second rows of the $C_{2\times4}$ CDW matrix are firstly divided into the left and right parts, respectively, to result in the following expression:

$$C_{2\times8} = \begin{bmatrix} a_{11} & a_{21} & a_{11} & -a_{21} & a_{12} & a_{22} & a_{12} & -a_{22} \\ a_{11} & a_{21} & -a_{11} & a_{21} & a_{12} & a_{22} & -a_{12} & a_{22} \end{bmatrix} = \begin{bmatrix} +1 & +1 & +1 & -1 & +1 & -1 & +1 & +1 \\ +1 & +1 & -1 & +1 & +1 & -1 & -1 & -1 \end{bmatrix} \quad (12)$$

Figure 3:
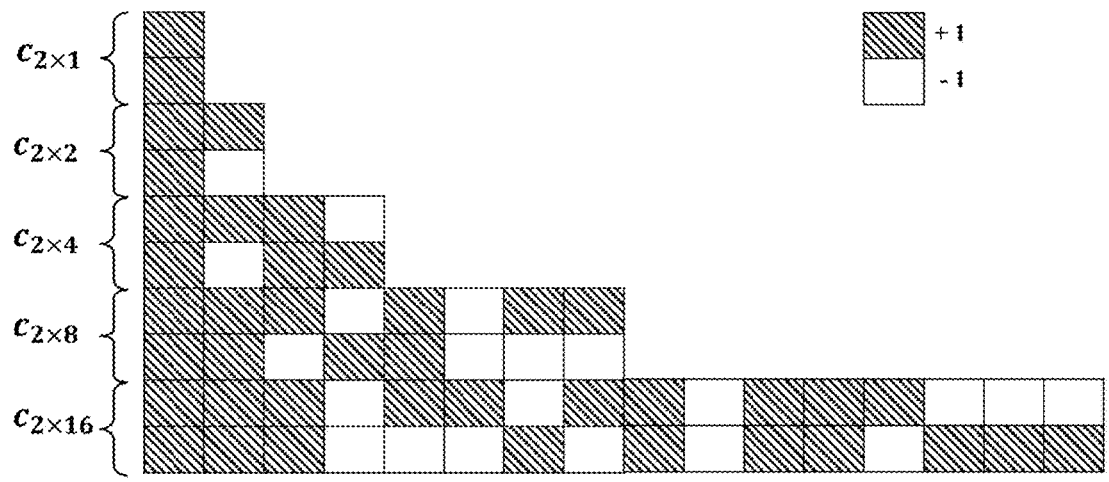
FIG. 3 shows an illustration of a designed CDW coding matrix with a length of 1, 2, 4, 8, and 16 according to an embodiment of the subject invention.

In addition, a $C_{2\times16}$ CDW matrix can be obtained from the $C_{2\times8}$ CDW matrix, and so on. In general, a $C_{2\times2^k}$ CDW matrix can be derived from the $C_{2\times2^{k-1}}$ CDW matrix with the similar coding procedure as shown in FIG. 2, where A represents the block matrix consisting of the left part of the first row, B represents the block matrix consisting of the right part of the first row, C represents the block matrix consisting of the left part of the second row, and D represents the block matrix consisting of the right part of the second row. FIG. 3 shows the designed CDW matrix with a length of $2^k$, where k is an integer.

Figure 4:
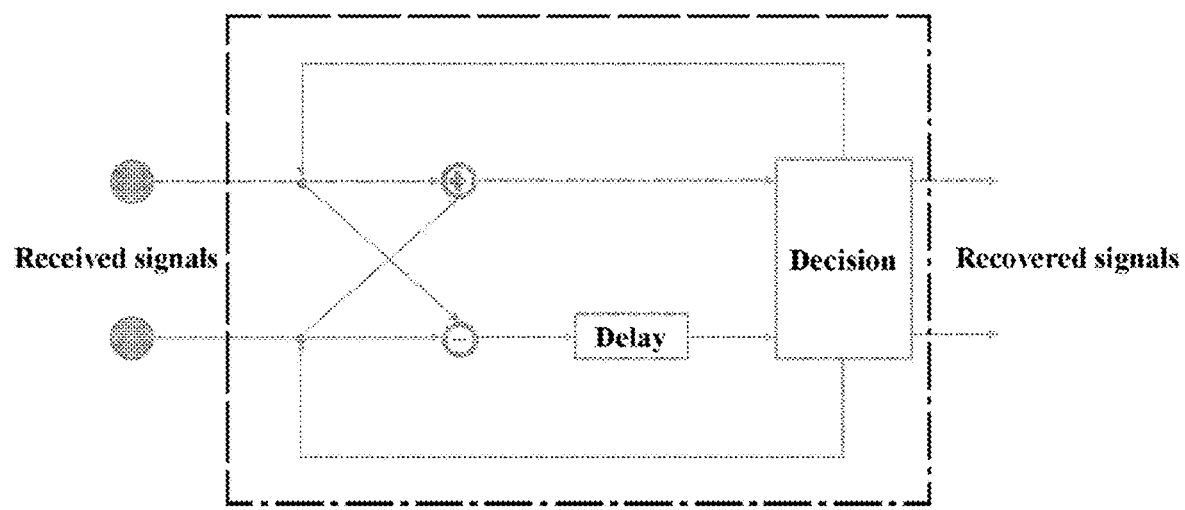
FIG. 4 shows an illustration of a decoding process for the CDW coding matrix according to an embodiment of the subject invention.

FIG. 4 shows the general decoding process. The decoder comprises of addition, subtraction, and delay operations. In the first loop, the received signals from two successive transmissions can be summed or subtracted, and then delayed to obtain the processed signals. A decider can be used to send the processed signals for the next loop or the final decoded output signals. The number of the loops is $L=\log_2(N)$ with N waves, and the delay for the l-th loop is:

$$\tau_l = \begin{cases} \tau, & 0 < l < L \\ (N/2) \cdot \tau, & l = L \end{cases} \quad (13)$$

Moreover, the described CDW coding and decoding theory can also be applied to M transmits, in which each of the two successive transmits could be processed based on the $C_{2\times N}$ CDW matrix.

The CDW imaging sequence design consists of the transmission and reception parts. On transmission, each transmitted signal can be a long pulse which contains N ($N=2^k$, k=0, 1, 2, ... ) cascaded waves with short time intervals and +1 or −1 polarity coefficients, instead of the conventional short pulse with a single wave. On reception, a linear decoding scheme comprised of addition, subtraction and delay operations is devised to recover N times higher intensity backscattered signals to gain SNR of $10 \cdot \log_{10}(N)$.

Figure 5:
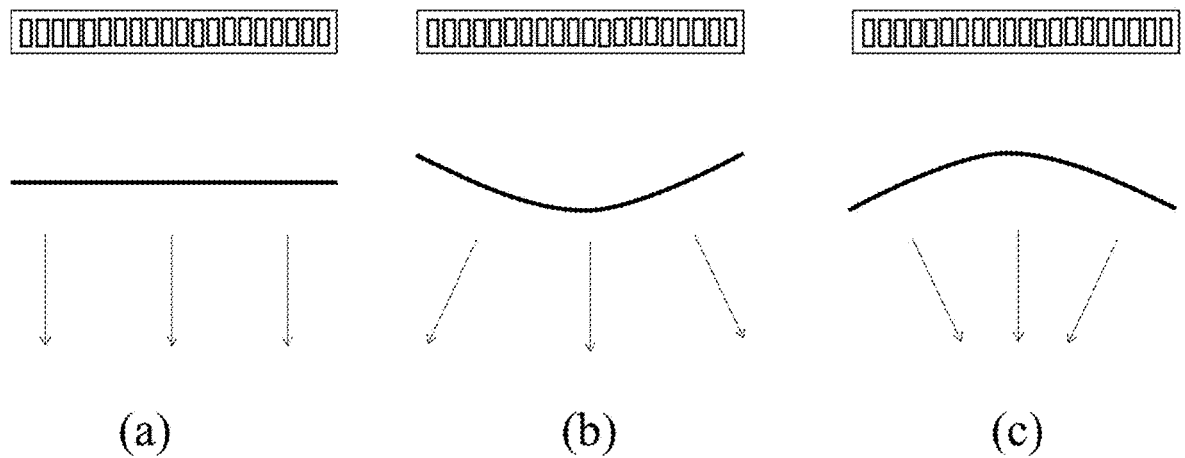
FIGS. 5(a)-5(c) show an illustration of the types of waves generated by an array compatible for CDW imaging with 5(a) being a plane wave, 5(b) being a diverging wave, and 5(c) being a focused wave.

The type of the wave of the CDW imaging can be the plane wave, diverging wave, focused wave, or other forms as shown in FIG. 5. A flat planar wavefront can be generated by simultaneously activating all the elements in the array, and a tilted planar wavefront can be generated by sequentially activating the elements in the array. A diverging wave can be generated by setting a virtual source behind the array. A focused wave can be generated by setting a focus in front of the array.

Embodiments of the subject invention can operate above and below a pulse repetition frequency (PRF) of 20,000 Hz. The PRF is the number of pulses (transmission and reception cycles) of waves sent out by the transducer per second. The PRF is dependent on the velocity of waves and on the depth of subject tissue being examined.

Figure 6:
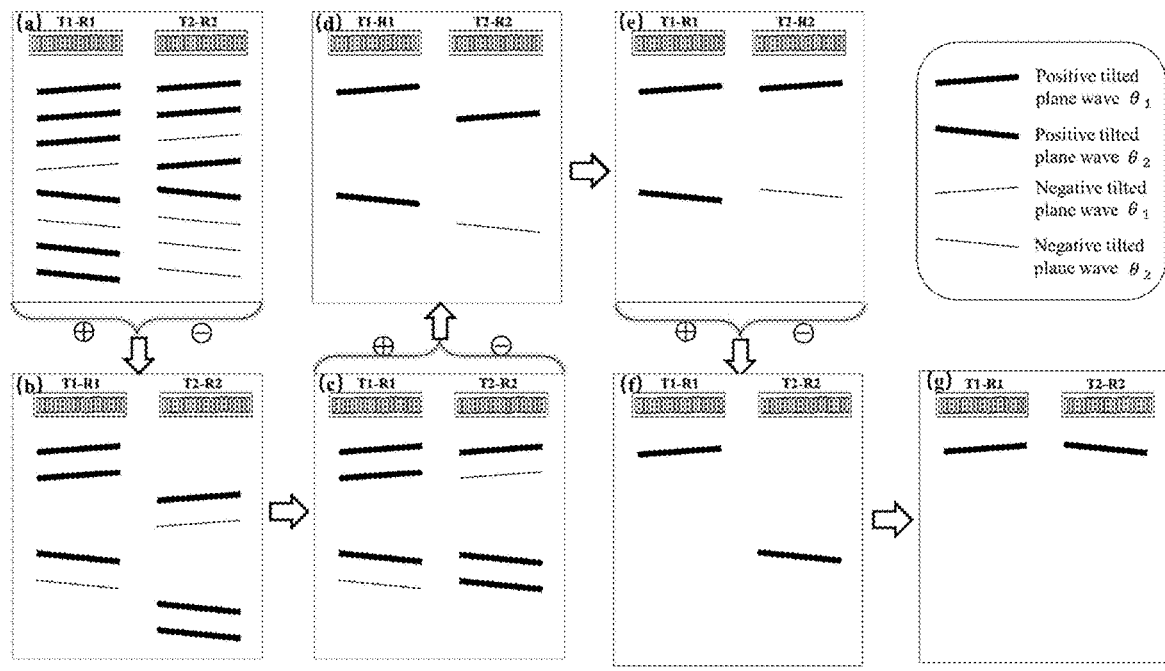
FIG. 6 shows an illustration of the 8 cascaded wave transmission sequence and reception decoding sequence design of the CDW imaging.

FIG. 6 shows a two-transmit sequence of CDW imaging with eight cascaded waves for each transmission. The diagram of the initially transmitted cascaded waves is shown in FIG. 6(a). In transmission, each transmitted signal is a long pulse which contains eight cascaded waves with short time intervals and +1 or −1 polarity coefficients. The $1^{st}$ to $4^{th}$ waves are tilted plane waves with a steering angle of $\theta_1$, and the $5^{th}$ to $8^{th}$ waves are tilted plane waves with a steering angle of $\theta_2$. The polarity coefficients are obtained from the designed CDW matrix. The polarity of the first transmit event T1 is [+1,+1,+1,−1,+1,−1,+1,+1], and the second transmit event T2 is [+1,+1,−1,+1,+1,−1,−1,−1].

In reception, received signals from each transmit event are acquired and called R1 and R2 signals. FIGS. 6(b)-(g) show a decoding process to recover eight times higher signals from the initially acquired signals. The decoding process can be explained as follows:

1) R1 and R2 signals with two-fold amplitude in FIG. 6(b) are obtained by the addition and subtraction of the initially R1 and R2 signals in FIG. 6(a), respectively. The coefficients of R1 and R2 in FIG. 6(b) are [+2,+2,0,0,+2,−2,0,0] and [0,0,+2,−2,0,0,+2,+2].

2) The R2 signal in FIG. 6(b) is delayed to obtain the R2 signal in FIG. 6(c). The coefficients of R1 and R2 in FIG. 6(c) are [+2,+2,0,0,+2,−2,0,0] and [+2,−2,0,0,+2,+2, 0,0].

3) Similar to the step (1), R1 and R2 signals with four-fold amplitude in FIG. 6(d) are obtained by the addition and subtraction of the R1 and R2 signals in FIG. 6(c). The coefficients of R1 and R2 in FIG. 6(d) are [+4,0,0,0,+4,0,0,0] and [0,+4,0,0,0,−4, 0,0].

4) Similar to the step (2), the R2 signal in FIG. 6(d) is delayed to obtain the R2 signal in FIG. 6(e). The coefficients of R1 and R2 in FIG. 6(e) are [+4,0,0,0,+4,0,0,0] and [+4,0,0,0,−4, 0,0,0].

5) Similar to the step (3), R1 and R2 signals with eight-fold amplitude in FIG. 6(f) are obtained by the addition and subtraction of the R1 and R2 signals in FIG. 6(e). The coefficients of R1 and R2 in FIG. 6(f) are [+8,0,0,0,0,0,0,0] and [0,0,0,0,+8, 0,0,0].

6) Similar to the step (4), the R2 signal in FIG. 6(f) is delayed to obtain the R2 signal in FIG. 6(g). The coefficients of R1 and R2 in FIG. 6(g) are [+8,0,0,0,0,0,0,0] and [+8,0, 0,0,0,0,0,0], each of which is equivalent to the 8-fold amplitude of the single wave transmission.

The two-transmit sequence can be extended to the M-transmit sequence. Such extension is similar to CPWC with M steering angles, where M is an even number and M>2. Each pair of the transmits, such as $(T_1, T_2)$, $(T_3, T_4)$, ..., $(T_k, T_{k+1})$, ... $(T_{M-1}, T_M)$ can be designed based on the two-transmit sequence. For example, both $T_k$ and $T_{k+1}$ consist of 8 cascaded waves with short time intervals. The $1^{st}$ to $4^{th}$ waves are tilted plane waves with a steering angle of $\theta_k$ and the $5^{th}$ to $8^{th}$ waves are tilted plane waves with a steering angle of $\theta_{k+1}$.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processer reads and executes the code and/or data stored on a computer-readable medium, the computer system and/or processer performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; system on chip (SOC); digital signal processing (DSP) chip; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

As used herein, the term "center frequency" refers to an emitted frequency of an ultrasound wave; the term "pulse repetition frequency" refers to a frame rate of an ultrasound wave; the term "sampling frequency" refers to a rate for discretizing continuous signals, which are returning/received ultrasound waves.

As used herein, the term "subject" includes, but is not limited to, animals, plants, and any other organism or entity. The subject can be a vertebrate, more specifically a mammal (e.g., a human, horse, pig, rabbit, dog, sheep, goat, non-human primate, cow, cat, guinea pig or rodent), a fish, a bird, a reptile or an amphibian. The subject can be an invertebrate, more specifically an arthropod (e.g. insects or crustaceans). The term does not denote a particular age or sex. Thus, adult and newborn subjects, as well as fetuses, whether male or female, are intended to be covered.

The subject invention includes, but is not limited to, the following exemplified embodiments.

Embodiment 1. A method for ultrasound imaging, the method comprising:

transmitting an incident signal towards an object of interest;

receiving sets of reflected signals from the object of interest; and decoding the reflected signals to recover an output, wherein the incident signal is a pulse wave comprised of sets of N number of titled cascaded waves, wherein $N=2^k$ and k being a integer, wherein the waves of the incident signal have predetermined polarities, and wherein decoding comprises summing, subtracting, and delaying operations on the reflected or backscattered waves to obtain a processed signal.

Embodiment 2. The method of embodiment 1, wherein each set of N waves contains at least two source signals.

Embodiment 3. The method according to embodiment 1, wherein a set of incident signal waves is expressed as follows:

$$\begin{cases} x_{s1}(t) = \sum_{i=1}^{2^{k-1}} a_{1i} \cdot s_1(t) * \delta(t-(i-1)\cdot\tau) + \\ \qquad \sum_{i=2^{k-1}+1}^{N} a_{1i} \cdot s_2(t) * \delta(t-(i-1)\cdot\tau) \\ x_{s2}(t) = \sum_{i=1}^{2^{k-1}} a_{2i} \cdot s_1(t) * \delta(t-(i-1)\cdot\tau) + \\ \qquad \sum_{i=2^{k-1}+1}^{N} a_{2i} \cdot s_2(t) * \delta(t-(i-1)\cdot\tau) \end{cases}$$

wherein each set of N waves contains two source signals, $s_1(t)$ and $s_2(t)$.

Embodiment 4. The method according to any of embodiments 1-3, wherein the polarities of the waves are determined as follows:

determining a number of waves, N, transmitted in the incident signal;

providing a 2×2 Hadamard matrix;

repeating the Hadamard matrix to obtain a 2×N first matrix;

providing a 2×N second matrix be taking each element in the 2×N first matrix to form a column vector and concatenating the N column vectors; and providing a 2×N third matrix by element wise multiplication of the 2×N first matrix and the 2×N second matrix.

Embodiment 5. The method according to any of embodiments 1-4, wherein an incident tilted wave is a plane wave, diverging wave, or a focused wave.

Embodiment 6. The method according to any of embodiments 1-5, wherein the object of interest is tissue of a subject.

Embodiment 7. The method according to any of embodiments 1-6, wherein the waves are emitted at a pulse repetition frequency below 20,000 Hz.

Embodiment 8. The method according to any of embodiments 1-6, wherein the waves are emitted at a pulse repetition frequency above 20,000 Hz.

Embodiment 9. A non-transitory machine readable storage medium comprising stored instruction thereon, the instructions when executed cause a processor to:

direct an array to transmit an incident signal towards an object of interest;

receive sets of reflected signals from the object of interest; and decode the reflected signals to recover an output, wherein the incident signal is a pulse wave comprised of sets of N number of titled cascaded waves, wherein $N=2^k$ and k being a integer, wherein the waves of the incident signal have predetermined polarities, and wherein decoding comprises summing, subtracting, and delaying operations on the reflected waves to obtain a processed signal.

Embodiment 10. The method according to embodiment 9, wherein the polarities of the waves are determined as follows:

determining a number of waves, N, transmitted in the incident signal;

providing a 2×2 Hadamard matrix;

repeating the Hadamard matrix to obtain a 2×N first matrix;

providing a 2×N second matrix be taking each element in the 2×N first matrix to form a column vector and concatenating the N column vectors; and providing a 2×N third matrix by element wise multiplication of the 2×N first matrix and the 2×N second matrix.

Embodiment 11. The method according to any of embodiments 9-10, wherein an incident tilted wave is a plane wave, diverging wave, or a focused wave.

Embodiment 12. The method according to any of embodiments 9-11, wherein the object of interest is tissue of a subject.

Embodiment 13. The method according to any of embodiments 9-12, wherein the waves are emitted at a pulse repetition frequency below 20,000 Hz.

Embodiment 14. The method according to any of embodiments 9-13, wherein the waves are emitted at a pulse repetition frequency above 20,000 Hz.

Embodiment 15. The method according to any of embodiments 9-14, wherein a decider is used to decide to repeat the adding, subtracting, and delay operations on the processed signal or to provide a final decoded output.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

The CDW imaging sequence was first tested with a point target (nylon wires immersed in water) at 21.8 mm away from the array. The data were acquired using a Verasonics Vantage system (Verasonics, Kirkland, Wash.) equipped with a linear array transducer ATL L11-4v whose transmit center frequency was 8.9 MHz. In the transmission, the 64th element was active to transmit eight cascaded waves with an added 1.2 µs short time interval. The polarity of each wave was obtained from the CDW matrix $C_{2\times8}$. Full aperture was used in reception.

Figure 7:
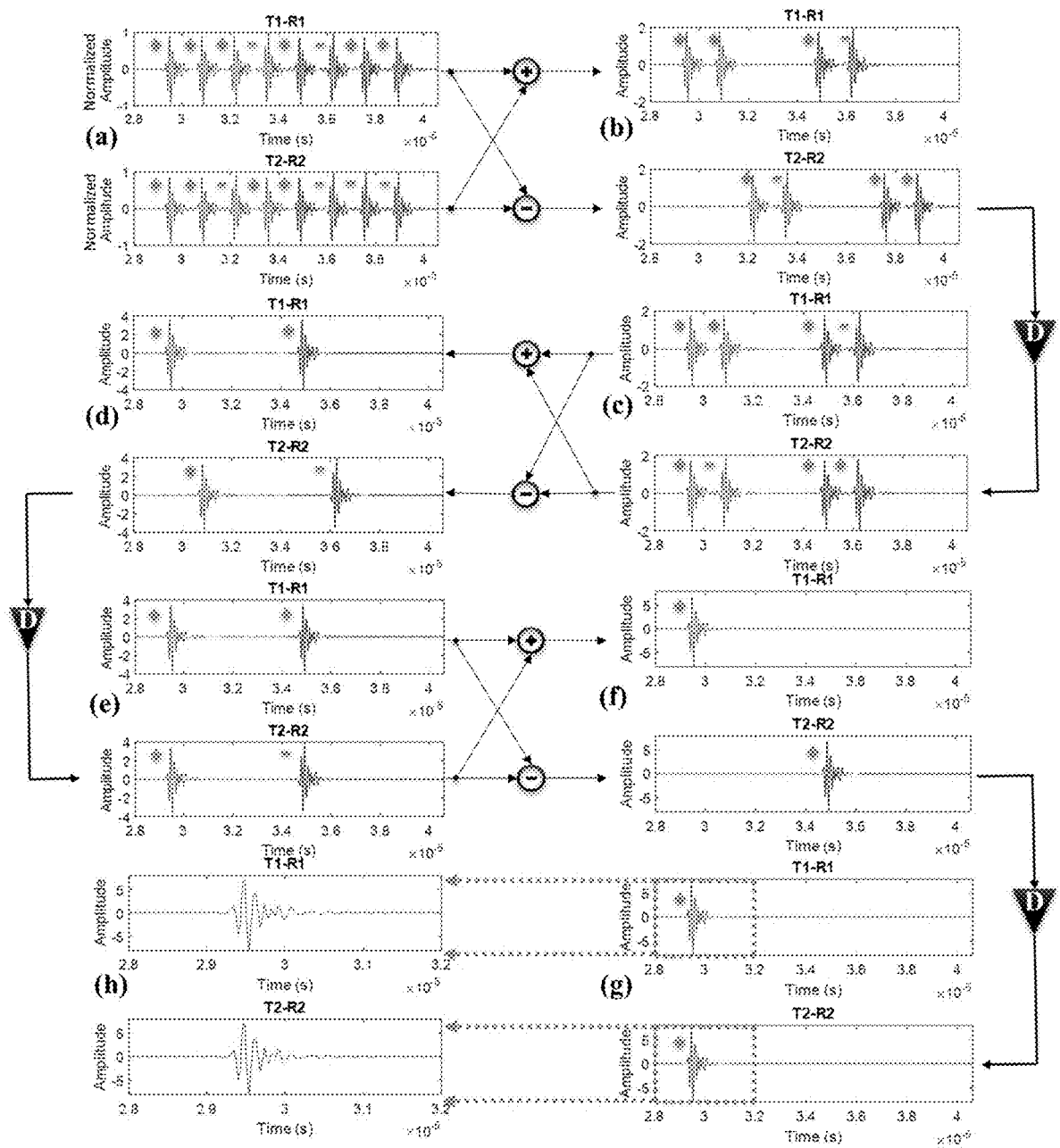
FIGS. 7(a)-7(h) shows plots of received signals from a wire phantom by two transmits with eight cascaded waves with 7(a) being initial received signals, 7(b)-7(g) being signals of each step in the decoding process, and 7(h) being the recovered signals.

The received signals from a wire phantom using eight cascaded waves for each transmit event are shown in FIG. 7(a). The received signals have eight wavefronts with different polarity coefficients for each transmit event because each transmission is comprised of eight cascaded dual-polarity waves. The 1st to 4th waves are one type of wave (in blue color), and the 5th to 8th waves are another type of wave (in red color). The polarities of the wavefronts in the first and second receptions are [+1,+1,+1,−1,+1,−1,+1,+1] and [+1,+1,−1,+1,+1,−1,−1,−1], respectively. They are the same as the designed CDW $C_{2\times8}$ matrix.

FIGS. 7(b)-(g) show the signals of each step of the decoding procedure. The aim of the decoding procedure is to separately recover the signals corresponding to the blue color and red color with an amplitude increase by eight fold. According to the previously described decoding steps (1)-(6), signals corresponding to the transmitted waves with blue color and red color were recovered as shown in FIG. 7(g) and FIG. 7(h), respectively. The amplitude of the recovered signal was eight-fold amplitude increase compared to the initially received signals in FIG. 7(a). Similarly, an N-fold amplitude increase can be obtained from N cascaded waves used for each transmission event.

Example 2

In medical ultrasound imaging, B-mode images are used to display the tissue anatomy. The CPWC, MW and CDW sequences were successively performed to ensure the same scanning region for comparisons. The two steered plane waves by the linear L11-4v probe (center frequency 8.9 MHz) were −2 degrees and 2 degrees. The azimuth of the image is from −19 mm to 19 mm. The compounded frame rate was 4000 fps. Sixteen cascaded waves with a 0.3 µs short time interval were generated for each transmission event. In addition, CPWC and MW imaging served as a reference. The experimental protocol of the back muscle was approved prior to use by the Institutional Review Board of the University of Hong Kong (UW 16-2012).

Quantitative evaluation metrics, such as spatial resolution, SNR, contrast ratio (CR), and contrast to noise ratio (CNR), and penetration depth were performed by 100 acquired images repeated with a fixed position of the imaging array probe, the phantom, and ex vivo pork belly. Axial and lateral resolutions were calculated by the full width half maximum (FWHM) of the profile around the strong reflector at approximately 22 mm depth inside the calibration phantom. For each A-line at different depths, the ratios of the mean and the standard deviation of the 100 repeated acquisitions were calculated as an indication of SNR. The SNR represents the strength of sonographic signals over electric noise because the mean indicates the real signals, while the standard deviation represents the noise. The final SNR was obtained by the mean SNR among several A-lines to increase the calculation robustness. The CR was calculated as CR=$|\mu_s-\mu_c|$, where $\mu_s$ and $\mu_c$ are the mean intensities of the regions of background and lesion/cyst, respectively. The CNR was calculated as CN=$|\mu_s-\mu_c|/\sqrt{\sigma_s^2+\sigma_c^2}$, where $\sigma_s$ and $\sigma_c$ are the intensity standard deviations of the background and lesion/cyst, respectively. The penetration depth was calculated from the depth where SNR dropped to the minimum and then stabilized in the calibration phantom.

Figure 8:
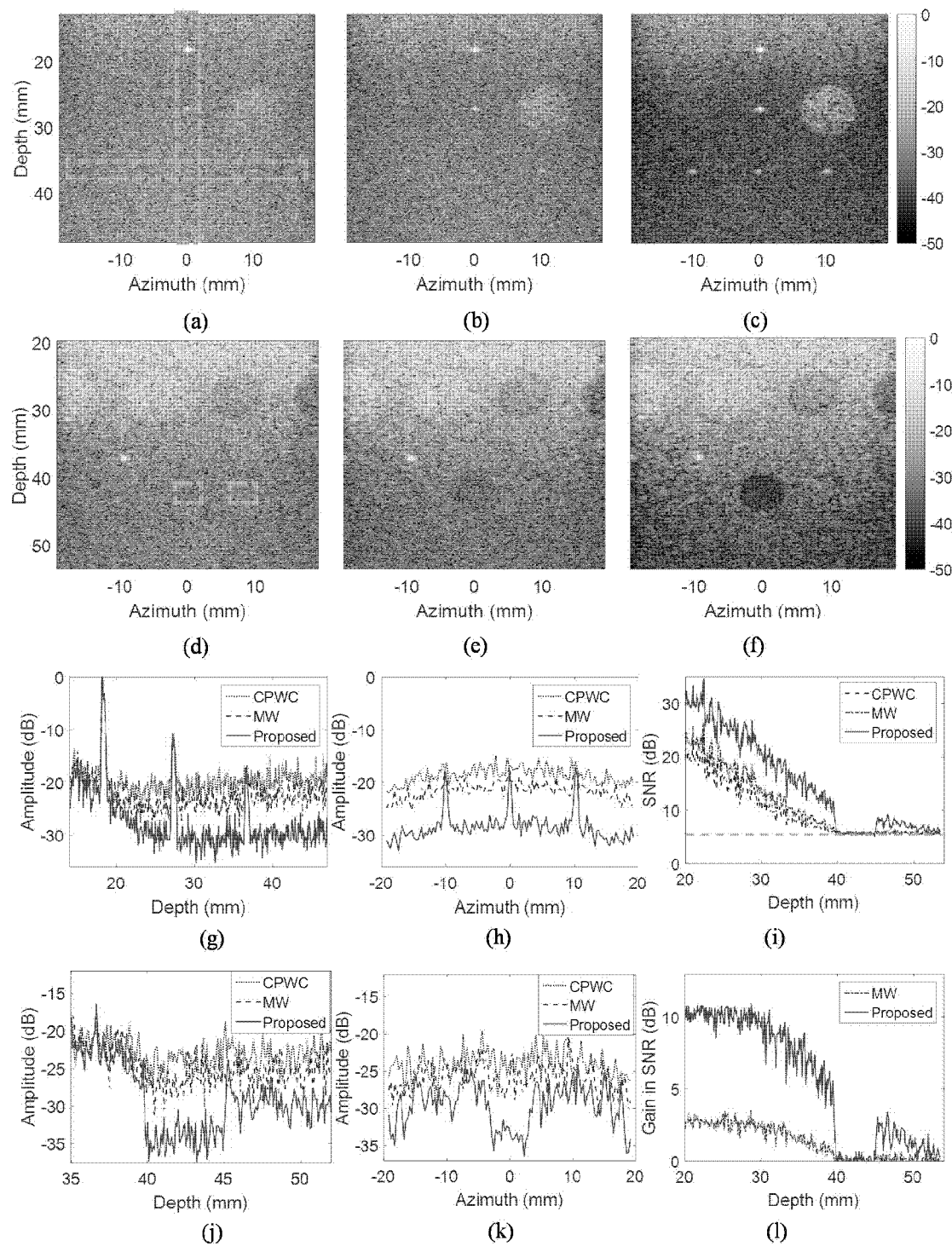
FIGS. 8(a)-8(c) shows B-mode images of a calibration phantom with strong reflectors with 8(a) being CPWC, 8(b) being MW, and 8(c) being CDW imaging.
FIGS. 8(d)-8(f) show B-mode images of a calibration phantom with cysts with 8(d) being CPWC, 8(e) being MW, and 8(f) being CDW imaging.
FIG. 8(g) shows a plot of axial profiles at azimuth 0 mm from 8(a)-8(c).
FIG. 8(h) shows a plot of lateral profiles from 8(a)-8(c) at depth 37.5 mm.
FIG. 8(i) shows a plot of lateral profiles from 8(d)-8(f) at depth 37.5 mm.
FIG. 8(j) shows a plot of axial profiles at azimuth 0 mm from 8(d)-8(f).
FIG. 8(k) shows a plot of lateral profiles from 8(d)-8(f) at depth 42.5 mm.
FIG. 8(l) shows a plot of the gain in SNR compared with CPWC at azimuth 0 mm from 8(d)-8(f).

FIG. 8 shows the B-mode images, axial and lateral profiles, and SNR of in vitro calibration phantom by CPWC, MW and proposed CDW imaging. FIGS. 8(a)-(c) show that CDW imaging enabled increased penetration depth and the best delineation of the strong reflectors, especially at the depth of 37.5 mm. The axial profile taken at azimuth 0 mm and the lateral profile at depth 37.5 mm (orange box in FIG. 8(a)) show that the suppression of the background noise level by CDW was approximately 10 dB more than that of CPWC and 8 dB more than that of MW imaging. FIGS. 8(d)-(f) show that the proposed CDW imaging demonstrated the best delineation of the cyst at a depth of 42.5 mm. The axial profile at azimuth 0 mm in FIG. 8(j) and the lateral profile at the depth of 42.5 mm show the suppression of the noise level in the cyst by CDW was approximately 10 dB more than that of CPWC and 8 dB more than that of MW imaging. The SNR at azimuth 0 mm from FIGS. 8(d)-(f) in FIG. 8(i) show that the SNR of CDW was much higher than that of CPWC and MW. The SNR gain evidenced in FIG. 8(1) shows that the SNR of the proposed CDW imaging was 10 dB and 7 dB higher than CPWC and MW imaging, respectively, in the near region.

improvement of SNR by proposed CDW imaging was 65.03% as compared with CPWC and 38.96% as compared with MW imaging. The penetration depth was calculated from the depth where SNR dropped to the minimum and remained around 6 dB as indicated by the blue dotted line in FIG. 8(i). The improvement of the penetration depth by proposed CDW imaging was 36.94% as compared with CPWC and 35.14% as compared with MW imaging.

Figure 9:
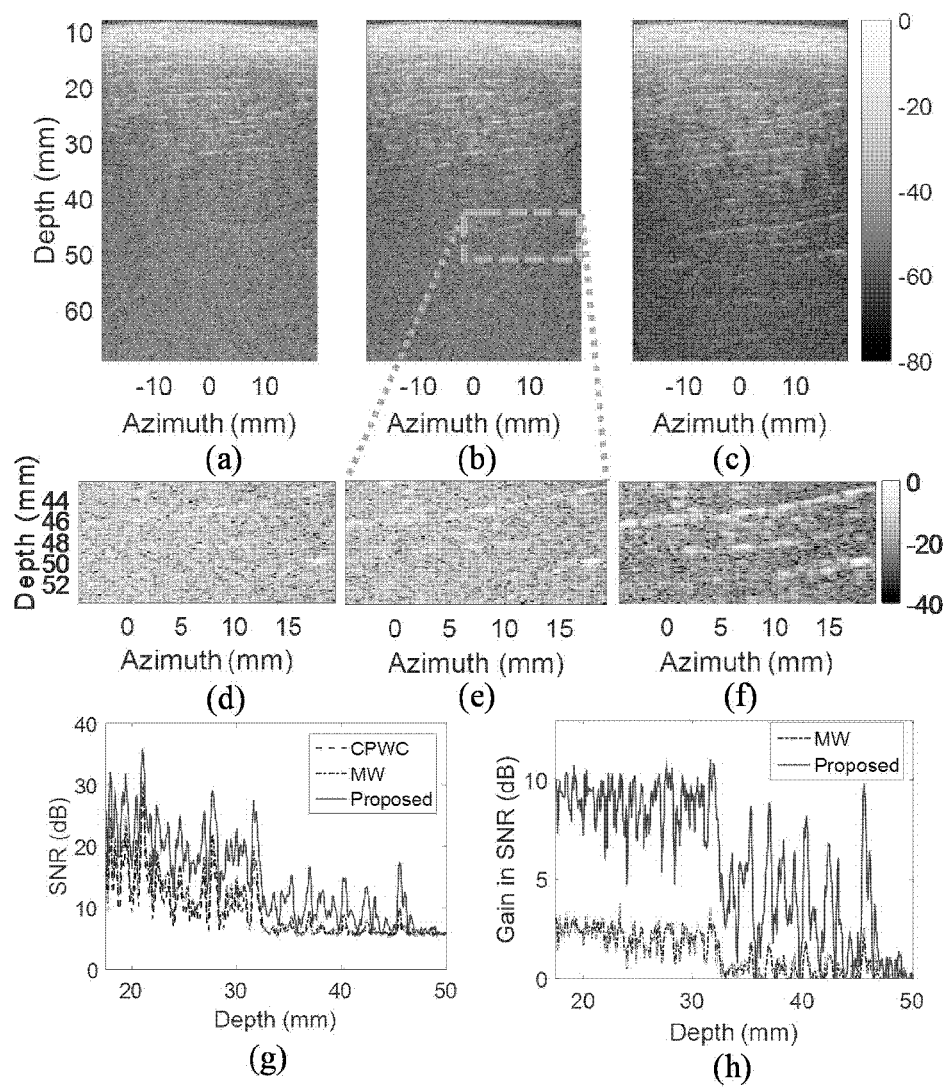
FIGS. 9(a) and 9(d) shows B-mode images of ex vivo pork belly using CPWC imaging.
FIGS. 9(b) and 9(e) shows B-mode images of ex vivo pork belly using MW imaging.
FIGS. 9(c) and 9(f) shows B-mode images of ex vivo pork belly using CDW imaging.
FIG. 9(g) shows a plot of the SNR along the axial direction at azimuth 0 mm.
FIG. 9(h) shows a plot of the gain of SNR along the axial direction.

FIG. 9 shows the B-mode images and SNR of ex vivo pork belly by CPWC, MW and proposed CDW imaging. FIGS. 9(a)-(c) show that the proposed CDW imaging enabled comparable delineation of the muscle fibers in the ROI shallower than 30 mm depth. However, CDW enabled enhanced delineation (i.e., much higher clarity and continuity) of the muscle fibers in FIGS. 9(d)-(f) at the depths from 42 mm to 52 mm. FIG. 9(g) shows that CDW exhibited much higher SNR at azimuth 0 mm than CPWC and MW. The gain of SNR in FIG. 9(h) shows that proposed CDW imaging increased around 10 dB in SNR compared with CPWC and 7 dB compared with MW imaging in the near zone.

Figure 10:
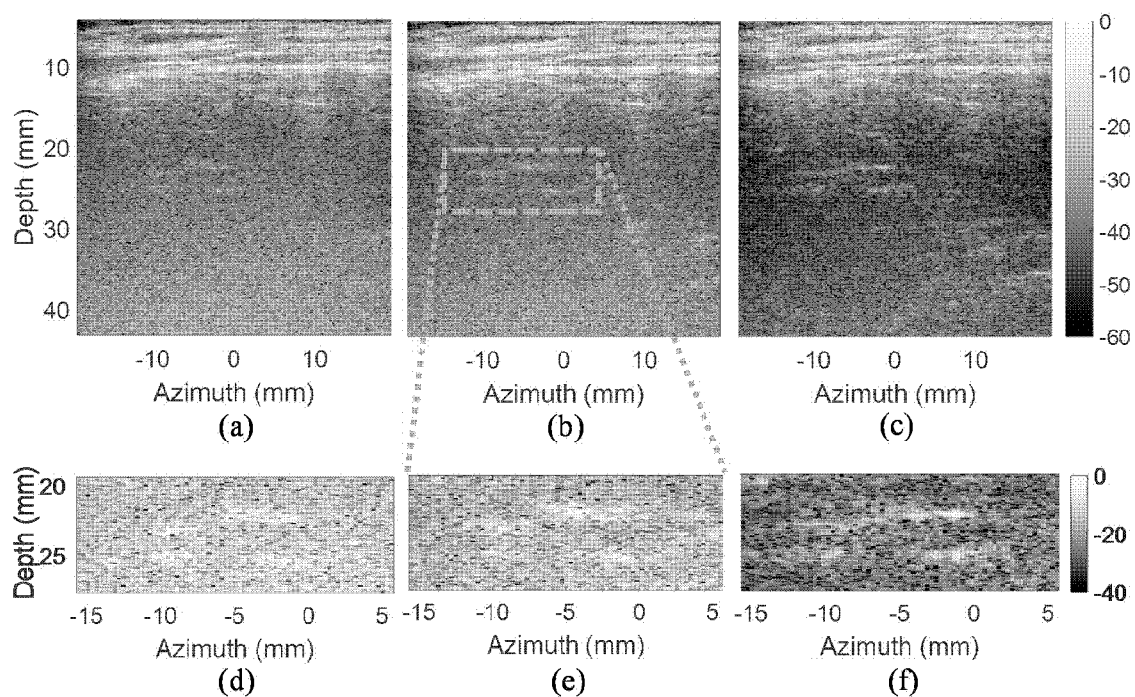
FIGS. 10(a) and 10(d) shows B-mode images of in vivo human back muscles using CPWC imaging.
FIGS. 10(b) and 10(e) shows B-mode images of in vivo human back muscles using MW imaging.
FIGS. 10(c) and 10(f) shows B-mode images of in vivo human back muscles using CDW imaging.
Figure 11:
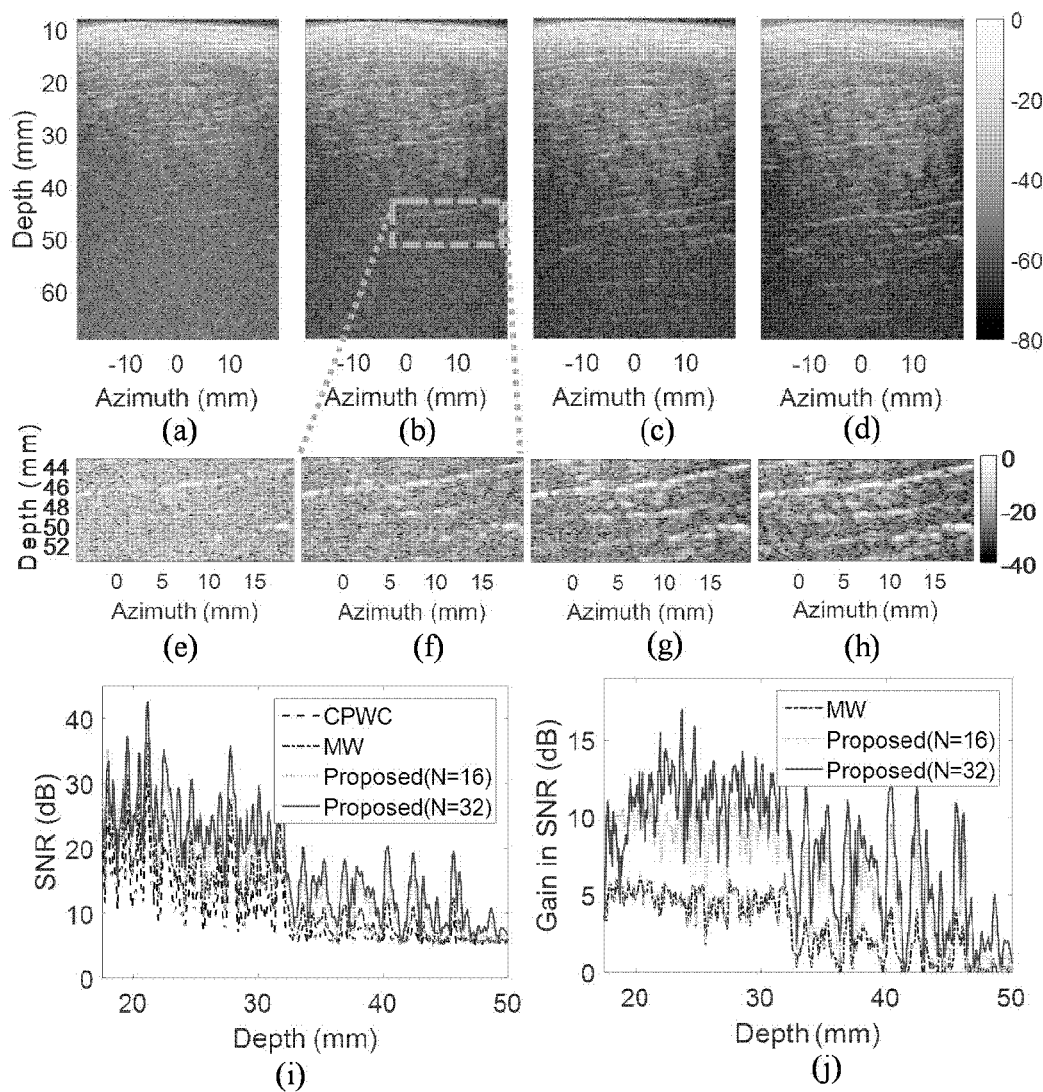
FIGS. 11(a) and 11(e) shows images of ex vivo pork belly meat with four compounded transmits (four steering angles) using CPWC imaging.
FIGS. 11(b) and 11(f) shows images of ex vivo pork belly meat with four compounded transmits (four steering angles) using MW imaging.
FIGS. 11(c) and 11(g) shows images of ex vivo pork belly meat with four compounded transmits (four steering angles) using CDW imaging with N=16.
FIGS. 11(d) and 11(h) shows images of ex vivo pork belly meat with four compounded transmits (four steering angles) using CDW imaging with N=32.
FIG. 11(i) shows a plot of the SNR along the axial direction at azimuth 0 mm.
FIG. 11(j) shows a plot of the gain of the SNR compared with CPWC along the axial direction.

FIG. 10 shows the B-mode images of in vivo human back muscle by CPWC, MW, and proposed CDW imaging. FIGS. 10(a)-(c) show that the proposed CDW imaging enabled comparable delineation of the back muscle fibers in the ROI shallower than 20 mm in depth. However, CDW enabled enhanced delineation of the structures in FIG. 10(d)-(f) at depths from 20 mm to 28 mm.

The aforesaid embodiments relate to the cascaded dual-polarity wave (CDW) model which is in the time domain for plane wave imaging.

The further embodiments of the subject invention provide a cascaded synthetic aperture imaging (CaSA) model which extends the CDW model into the spatial-temporal domain. The CaSA scheme improves ultrafast ultrasound image

TABLE I

| COMPARISONS OF RESOLUTION, CONTRAST, SNR, PENETRATION AND FRAME RATE | | | | | |
|---|---|---|---|---|---|
| Symbol | CPWC | MW | Proposed CDW | Proposed CDW compared to CPWC | Proposed CDW compared to MW |
| Axial resolution (mm) | 0.45 ± 0.028 | 0.43 ± 0.015 | 0.43 ± 0.006 | (+4.4%) | (+0%) |
| Lateral resolution (mm) | 0.54 ± 0.018 | 0.53 ± 0.011 | 0.53 ± 0.005 | (+1.9%) | (+0%) |
| CR (dB) | 0.78 ± 0.491 | 1.70 ± 0.532 | 6.75 ± 0.456 | (+765.4%) | (+297.1%) |
| CNR (dB) | 0.12 ± 0.076 | 0.27 ± 0.084 | 0.97 ± 0.068 | (+708.3%) | (+259.3%) |
| SNR (dB) | 16.47 | 19.56 | 27.18 | (+65.03%) | (+38.96%) |
| Penetration depth (mm) | 38.98 | 39.50 | 53.38 | (+36.94%) | (+35.14%) |
| Frame rate (fps) | 4000 | 4000 | 4000 | (+0%) | (+0%) |

Table I shows the axial and lateral resolutions, CR, CNR, SNR, penetration depth and the frame rate of CPWC, MW and CDW imaging. Axial and lateral resolutions were calculated at depth 18 mm and azimuth 0 mm from FIGS. 8(a)-(c). Our proposed CDW imaging exhibited comparable spatial resolution to MW and CPWC but the lowest standard variation. CR and CNR were calculated at depth 42.5 mm and azimuth 0 mm from the region of interest (ROI) indicated in orange color in FIG. 8(d). The proposed CDW presented significant improvement of the CR and CNR compared with CPWC and MW imaging in deep regions. The improvement of CR by proposed CDW imaging was 765.4% as compared with CPWC and 297.1% as compared with MW imaging. The improvement of CNR by proposed CDW imaging was 708.3% as compared with CPWC and 259.3% as compared with MW imaging. The SNR value was selected from the depth at 26.48 mm in FIG. 8(i). The quality through encoding in both temporal and spatial domains and may be applied to all types of ultrasound array probes (e.g., linear array, phased array, and curvilinear array).

In the CaSA scheme, the signals for M transmission-reception events may be given by:

$$X_C = \begin{bmatrix} X_1 \\ X_2 \\ \vdots \\ X_M \end{bmatrix} = \begin{bmatrix} x_{11}(t) & x_{12}(t) & \cdots & x_{1M}(t) \\ x_{21}(t) & x_{22}(t) & \cdots & x_{2M}(t) \\ \vdots & \vdots & \vdots & \vdots \\ x_{M1}(t) & x_{M2}(t) & \cdots & x_{MM}(t) \end{bmatrix} \quad (14)$$

where $X_1, X_2, \ldots, X_M$ represent the transmitted signals for the $1^{th}, 2^{rd}, \ldots, M^{th}$ transmission-reception events, and $x_{11}(t), x_{1M}(t), \ldots, x_{MM}(t)$ represent the transmitted signals from the subarrays. The transmitted signals in the $m^{th}$ transmission and $n^{th}$ subarray are given by $$x_{mn}(t)=\Sigma_{i=1}^{N}c_{li} \cdot s_n(t)*\delta(t-(i-1)\cdot\tau) \quad (15)$$

where $s_n(t)$ is the source signal of the $n^{th}$ subarray, $\tau$ is the preset delay added between waves, $c_{li}$ is the coefficients of each cascaded wave, $\delta$ is the delta function.

In order to decode the received signals, there is a need to design a new matrix as the coefficients of the cascaded waves. FIG. 13 illustrates a design of the matrix $C_N H_M$ from $C_{N}H_{M}$ from $C_{2 \times N}$ and $H_{M \times M}$, wherein the previous $C_{2 \times N}$ matrix may be extended to a new matrix $C_N H_M$ with more than 2 rows based on the Hadamard matrix $H_{M \times M}$. For example, $C_8 H_2$ may be designed from $C_{2 \times 8}$ and $H_{2 \times 2}$ in the following steps:

1) The previous designed $C_{2 \times 8}$ matrix is $$C_{2\times 8}=\begin{bmatrix}+1 & +1 & +1 & -1 & +1 & -1 & +1 & +1 \\ +1 & +1 & -1 & +1 & +1 & -1 & -1 & -1\end{bmatrix} \quad (16)$$

2) Four block representations of the $C_{2 \times 8}$ matrix can be written as:

$$\begin{cases}C_{11}=[+1 \quad +1 \quad +1 \quad -1] \\ C_{12}=[+1 \quad -1 \quad +1 \quad +1] \\ C_{21}=[+1 \quad +1 \quad -1 \quad +1] \\ C_{22}=[+1 \quad -1 \quad -1 \quad -1]\end{cases}, \quad (17)$$

where $C_{11}$ and $C_{12}$ are the block matrices of the left and right parts of the first row, and $C_{21}$ and $C_{22}$ are the block matrices of the left and right parts of the second row.

3) It is known that the Hadamard matrix $H_{2 \times 2}$ is $$H_{2\times 2}=\begin{bmatrix}+1 & +1 \\ +1 & -1\end{bmatrix}. \quad (18)$$

4) Two block representations of the $H_{2 \times 2}$ may be written as $$\begin{cases}H_1=[+1 \quad +1] \\ H_2=[+1 \quad -1]\end{cases} \quad (19)$$

5) The multiplications of the transpose of $H_1$, $H_2$ and $C_{11}$, $C_{12}$, $C_{21}$, $C_{22}$ may be obtained as:

$$\begin{cases}H_1^T \cdot C_{11}=\begin{bmatrix}+1 & +1 & +1 & -1 \\ +1 & +1 & +1 & -1\end{bmatrix} \\ H_2^T \cdot C_{12}=\begin{bmatrix}+1 & -1 & +1 & +1 \\ -1 & +1 & -1 & -1\end{bmatrix} \\ H_1^T \cdot C_{21}=\begin{bmatrix}+1 & +1 & -1 & +1 \\ +1 & +1 & -1 & +1\end{bmatrix} \\ H_2^T \cdot C_{22}=\begin{bmatrix}+1 & -1 & -1 & -1 \\ -1 & +1 & +1 & +1\end{bmatrix}\end{cases} \quad (20)$$

6) The designed $C_8 H_2$ can be expressed as:

$$C_8 H_2=\begin{bmatrix}H_1^T \cdot C_{11} & H_2^T \cdot C_{12} \\ H_1^T \cdot C_{21} & H_2^T \cdot C_{22}\end{bmatrix}= \quad (21)$$

$$\begin{bmatrix}+1 & +1 & +1 & -1 & +1 & -1 & +1 & +1 \\ +1 & +1 & +1 & -1 & -1 & +1 & -1 & -1 \\ +1 & +1 & -1 & +1 & +1 & -1 & -1 & -1 \\ +1 & +1 & -1 & +1 & -1 & +1 & +1 & +1\end{bmatrix}$$

Similar to the design of $C_8 H_2$ matrix, the $C_8 H_4$ matrix can be obtained from the $C_{2 \times 8}$ and $H_{4 \times 4}$ matrices. It is known that the Hadamard matrix $H_{4 \times 4}$ and its block representation is $$H_{4\times 4}=\begin{bmatrix}H_1 \\ H_2 \\ H_3 \\ H_4\end{bmatrix}=\begin{bmatrix}+1 & +1 & +1 & +1 \\ +1 & -1 & +1 & -1 \\ +1 & +1 & -1 & -1 \\ +1 & -1 & -1 & +1\end{bmatrix} \quad (22)$$

Thus the $C_8 H_4$ matrix can be written as $$C_8 H_4=\begin{bmatrix}H_1^T \cdot C_{11} & H_2^T \cdot C_{12} \\ H_1^T \cdot C_{21} & H_2^T \cdot C_{22} \\ H_3^T \cdot C_{11} & H_4^T \cdot C_{12} \\ H_3^T \cdot C_{21} & H_4^T \cdot C_{22}\end{bmatrix}. \quad (23)$$

Based on the procedures in FIG. 13, the arbitrary $C_N H_M$ matrix may be obtained as:

$$C_N H_M=\begin{bmatrix}H_1^T \cdot C_{11} & H_2^T \cdot C_{12} \\ H_1^T \cdot C_{21} & H_2^T \cdot C_{22} \\ H_3^T \cdot C_{11} & H_4^T \cdot C_{12} \\ H_3^T \cdot C_{21} & H_4^T \cdot C_{22} \\ \vdots & \vdots \\ H_{M-1}^T \cdot C_{11} & H_M^T \cdot C_{12} \\ H_{M-1}^T \cdot C_{21} & H_M^T \cdot C_{22}\end{bmatrix}. \quad (24)$$

where $H_1^T, H_2^T, \ldots, H_M^T$ are the transpose of the rows of Hadamard matrix $H_{M \times M}$. The dimension of the matrix is $M^2 \times N$.

The process for application of the designed matrix to the model is provided hereinafter. According to the designed matrix $C_N H_M$ and the proposed cascaded model, the index $l$ of the $c_{li}$ is $$l=(m-1) \cdot M+k \quad (25)$$

Figure 12:
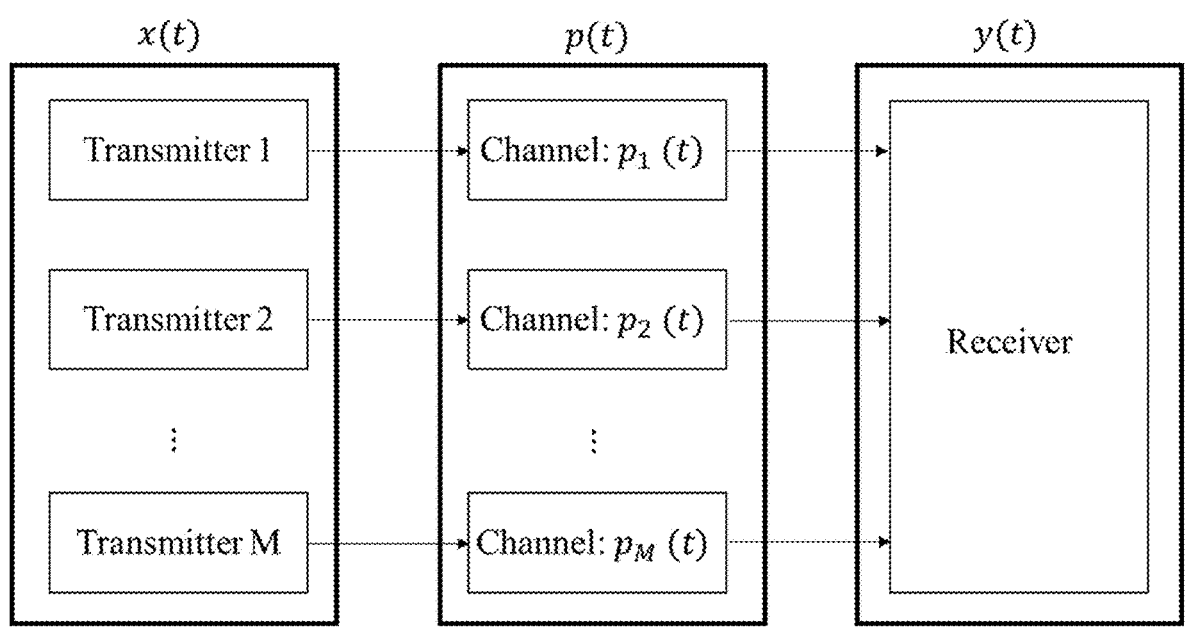
FIG. 12 shows an example of transmitter and receiver model for sub-aperture transmissions and full-aperture reception.

The received signals from each transmission-reception event as shown in FIG. 12 for CaSA model can be obtained as $$Y_C = \begin{bmatrix} y_{C1}(t) \\ y_{C2}(t) \\ \vdots \\ y_{CM}(t) \end{bmatrix} = \begin{bmatrix} \sum_{k=1}^{M} x_{1k} * p_k(t) + n_{C1}(t) \\ \sum_{k=1}^{M} x_{2k} * p_k(t) + n_{C2}(t) \\ \vdots \\ \sum_{k=1}^{M} x_{Mk} * p_k(t) + n_{CM}(t) \end{bmatrix} \quad (26)$$

where * denote the convolution operation, $n_{C1}(t)$, $n_{C2}(t)$, ..., $n_{CM}(t)$ are the noise for each received signals $y_{C1}(t)$, $y_{C2}(t)$, ..., $y_{CM}(t)$, $x_{Mk}$ is the transmitted signal from the k-th sub-aperture in the $M^{st}$ transmission-reception event, and $p_k(t)$ represents the system impulse response of the k-th sub-aperture. The received signals consist of the signals from each source signals.

According to equations (15) and (26), the received signals are expressed as:

$$Y_C = \begin{bmatrix} y_{C1}(t) \\ y_{C2}(t) \\ \vdots \\ y_{CM}(t) \end{bmatrix} = \quad (27)$$

$$\begin{bmatrix} \sum_{k=1}^{M} \left( \sum_{i=1}^{N} c_{ki} \cdot y_{Ok}(t) * \delta(t-(i-1)\cdot\tau) \right) + n_{C1}(t) \\ \sum_{k=1}^{M} \left( \sum_{i=1}^{N} c_{(M+k)i} \cdot y_{Ok}(t) * \delta(t-(i-1)\cdot\tau) \right) + n_{C2}(t) \\ \vdots \\ \sum_{k=1}^{M} \left( \sum_{i=1}^{N} c_{((M-1)\cdot M+k)i} \cdot y_{Ok}(t) * \delta(t-(i-1)\cdot\tau) \right) + n_{CM}(t) \end{bmatrix}$$

where $y_{Ok}(t)$ is the noise-free part of the received signals, and k indicates the k-th transmission-reception event.

The received signals consist of the signals from each source signals and the delay of source signals. Next, a decoding procedure need to be designed to recover the signals which is equivalent to the received signals from the SA model.

Figure 14:
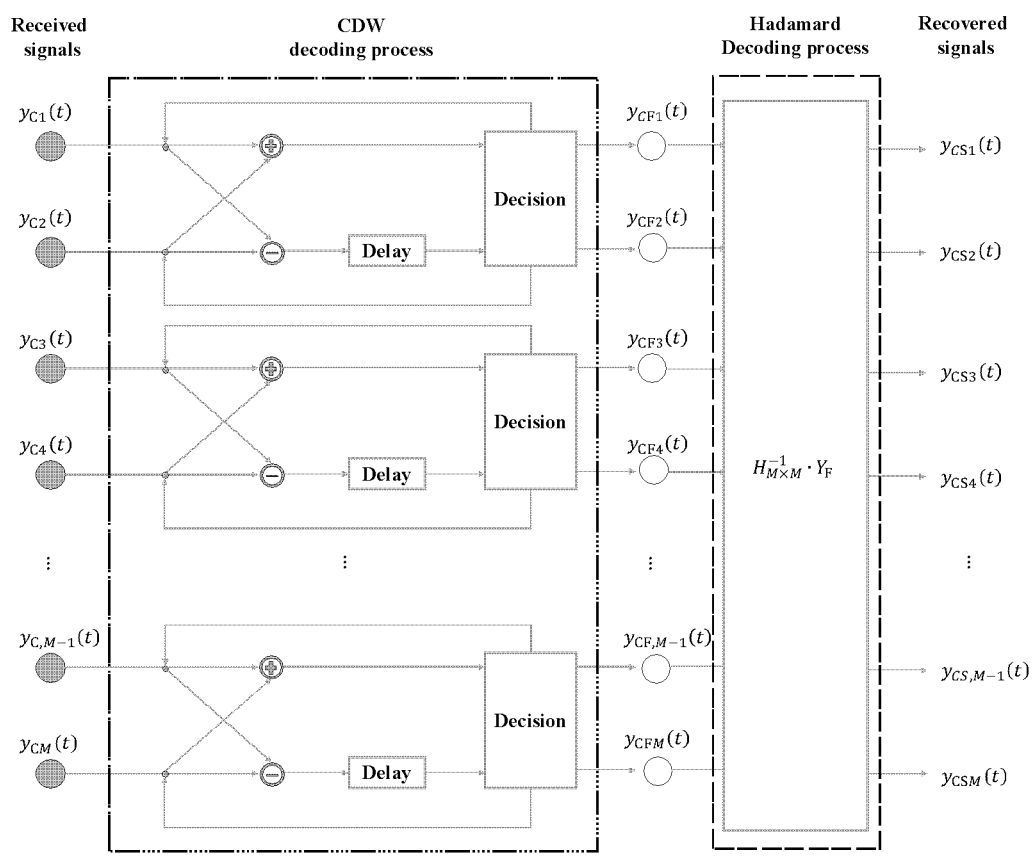
FIG. 14 shows a design of the decoding process in the cascaded synthetic aperture imaging (CaSA) model.

The design of the decoding process of the model is illustrated in FIG. 14. As shown in FIG. 14, the decoding process can be divided into two steps. After receiving the signals $y_{C1}(t)$, $y_{C2}(t)$, ..., $y_{CM}(t)$ from M transmission-reception events, each pair of them are utilized to obtain the decoded signals $y_{CF1}(t)$, $y_{CF2}(t)$, ..., $y_{CFM}(t)$ based on the previously designed CDW decoding process. Assuming the noise is AGWN (Additive White Gaussian Noise), the CDW decoded signal is $$Y_{CF} = \begin{bmatrix} y_{CF1}(t) \\ y_{CF2}(t) \\ \vdots \\ y_{CFM}(t) \end{bmatrix} = \quad (28)$$

$$N \cdot H_{M \times M} \cdot Y_O + N_M = \begin{bmatrix} N \cdot \sum_{k=1}^{M} a_{1k} \cdot s_k(t) * p_k(t) + \sum_{n=1}^{N} n_{1n}(t) \\ N \cdot \sum_{k=1}^{M} a_{1k} \cdot s_k(t) * p_k(t) + \sum_{n=1}^{N} n_{2n}(t) \\ \vdots \\ N \cdot \sum_{k=1}^{M} a_{1k} \cdot s_k(t) * p_k(t) + \sum_{n=1}^{N} n_{Mn}(t) \end{bmatrix}$$

where $N_M$ represents the matrix of summation of AGWN noise, $H_{M \times M}$ is the Hadamard matrix, N is the number of cascaded waves, and $a_{1k}$ represents the coefficients of the signals with a given value of −1 or +1 from the Hadamard matrix.

Then the final decoded signals can be obtained by the Hadamard decoding process. The final decoded signals are $$Y_{CS} = \begin{bmatrix} y_{CS1}(t) \\ y_{CS2}(t) \\ \vdots \\ y_{CSM}(t) \end{bmatrix} = \quad (29)$$

$$N \cdot Y_O + \frac{1}{M} \cdot H_{M \times M} \cdot N_M = \begin{bmatrix} N \cdot s_1(t) * p_1(t) + \frac{1}{M} \sum_{m=1}^{M} \sum_{n=1}^{N} n_{mn}(t) \\ N \cdot s_2(t) * p_2(t) + \frac{1}{M} \sum_{m=1}^{M} \sum_{n=1}^{N} n_{mn}(t) \\ \vdots \\ N \cdot s_k(t) * p_k(t) + \frac{1}{M} \sum_{m=1}^{M} \sum_{n=1}^{N} n_{mn}(t) \end{bmatrix}$$

where $p_1(t)$, $p_2(t)$, ..., $p_M(t)$ represent the impulse response of the wave propagation channels corresponding to the source signals $s_1(t)$, $s_2(t)$, ..., $s_M(t)$.

Since the noise is AGWN, thus the variance of the noise for each decoded received signals are $$\sigma_{CS} = \begin{bmatrix} N \cdot \sigma^2/M \\ N \cdot \sigma^2/M \\ \vdots \\ N \cdot \sigma^2/M \end{bmatrix}, \quad (30)$$

Thus, the SNR of the received signals for each transmission-reception event are $$SNR_{FS} = M \cdot N \cdot SNR_S = \begin{bmatrix} M \cdot N \cdot \mu_{yO1}^2/\sigma^2 \\ M \cdot N \cdot \mu_{yO2}^2/\sigma^2 \\ \vdots \\ M \cdot N \cdot \mu_{yOM}^2/\sigma^2 \end{bmatrix} \quad (31)$$

where $\mu_{y_{O1}}$, $\mu_{y_{O2}}$, ..., $\mu_{y_{OM}}$ are the mean value of the received signal from the $1^{th}$, $2^{rd}$, ..., $M^{th}$ transmission-reception events, and $\sigma^2$ is the variance of the noise.

Theoretically, the proposed CaSA model can increase the SNR by $10 \cdot \log_{10}(N \cdot M)$ compared with the conventional SA model and can increase the SNR by $10 \cdot \log_{10}(N)$ compared with the H-SA model.

The uCUS imaging sequence with CaSA for the heart consists of two parts: transmission and reception. To achieve a large FOV (>90 degrees), diverging, instead of plane waves, are transmitted. Diverging waves are emitted by virtually creating a source behind the imaging array. The delay of each array element concerned is set by the signal propagation time from the virtual source to the array element. A sub-aperture diverging wave is obtained by activating partial elements of the array and set a virtual source in the center. In order to solve the tradeoff between the spatial resolution and the length of transmitted waves, a matrix of sub-aperture divergent cascaded dual-polarity waves (CDW) with short time intervals and +1 or −1 polarity coefficients are transmitted. This method is named by the inventor as "cascaded synthetic aperture imaging (CaSA)". Different from the previous planar CDW imaging, a new spatiotemporal coding matrix $C_N H_M$ is designed based on the Hadamard matrix and the CDW matrix for the polarity coefficients of the waves from each sub-aperture, where M is the number of sub-apertures in the spatial domain and N is the number of cascaded waves in the temporal domain. In reception, a two-stage decoding scheme comprised of the temporal (CDW) decoding and the spatial (Hadamard) decoding is devised to recover NM times higher intensity echoes to gain SNR of $10 \times \log_{10}(N \times M)$. The high SNR echoes are then beamformed and processed to obtain the heart dynamics information.

Figure 15:
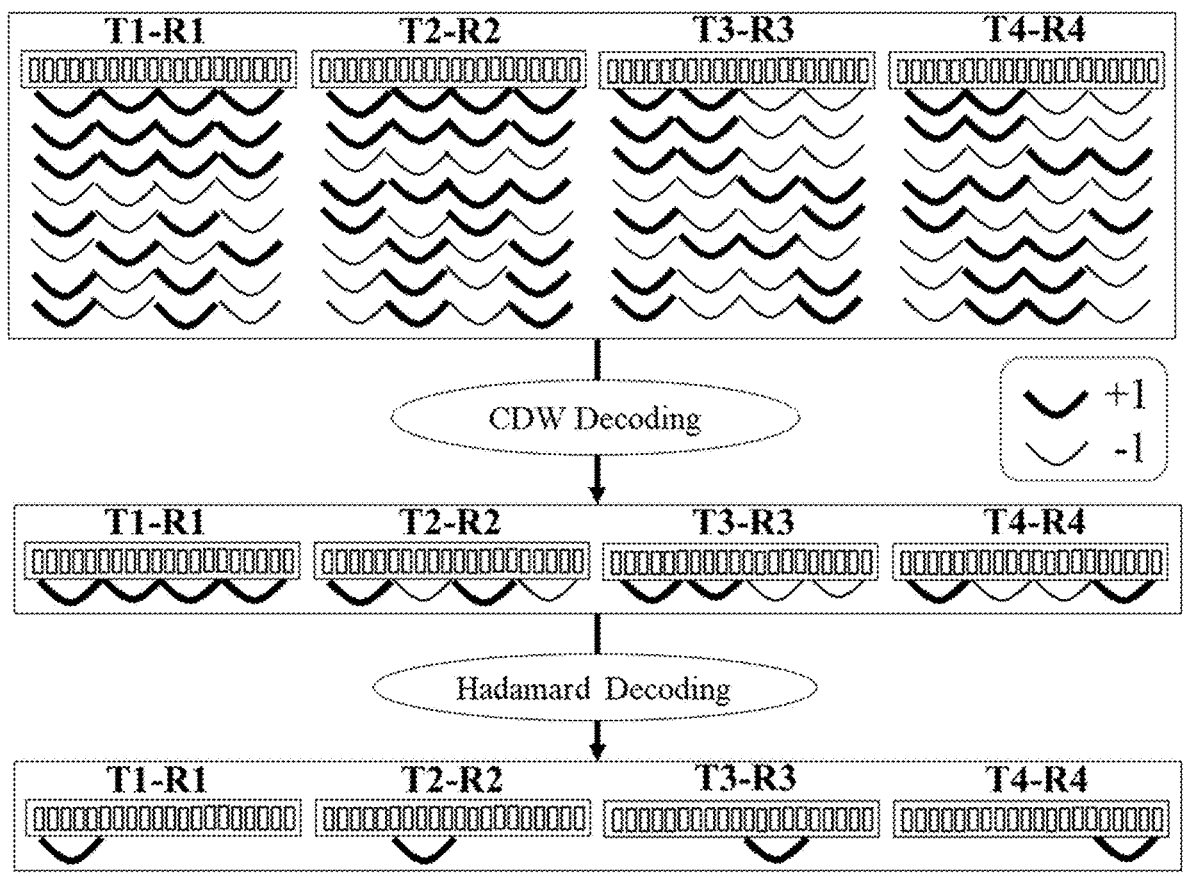
FIG. 15 illustrates an example of the four sub-aperture transmission with eight cascaded waves sequence and the corresponding reception decoding design of the CaSA.

In order to elucidate the proposed CaSA method for M transmission-reception events and N cascaded waves, four (M=4) transmission-reception events and eight (N=8) cascaded waves are exemplified in FIG. 15. In transmission, the array is equally divided into four sub-apertures; each sub-aperture transmits eight cascaded diverging waves with a guaranteed short time interval between two successive sets of cascaded waves. T1-R1, T2-R2, T3-R3, and T4-R4 indicate the $1^{st}$, $2^{nd}$, $3^{rd}$, and $4^{th}$ transmission-reception events. Therefore, in each transmission-reception event, a group of 32 diverging waves coded in both the spatial (columns) and temporal (rows) domains are transmitted. The positive (solid lines in FIG. 15) and negative (dotted lines in FIG. 15) coefficients are obtained from the designed coefficient matrix $C_8 H_4$ as explained above. The coefficients of the waves for T1-R1, T2-R2, T3-R3, and T4-R4 events are obtained from the $1^{st}$ to $4^{th}$ row, $5^{th}$ to $8^{th}$ row, $9^{th}$ to $12^{th}$ row, and $13^{th}$ to the $16^{th}$ row of the coefficient matrix $C_8 H_4$, respectively.

In reception, the full aperture of the array is deployed to receive the backscattered signals in each transmission-reception event. The received R1, R2, R3, and R4 signals form two-dimensional (2-D) matrices. A two-stage decoding process is directly applied to the four received signals—R1, R2, R3, and R4. At the first stage, the temporal CDW decoding process as described above is applied to obtain received signals with an N-fold increase—R1', R2', R3', and R4'. A spatial Hadamard decoding process is thereafter applied to obtain the final decoded signals with an N×M-fold increase in the amplitude. The decoded signals are lastly beamformed and coherently compounded to obtain one high SNR beamformed image frame.

The incident signals used in the CaSA method do not have to be titled. For the linear array application, the incident signals may be tilted, while for phased array applications, the ultrasound array probe may be divided into several sub-apertures, and the diverging wave transmissions in the phrased array applications may be tilted or not, which may depend on the functional information of biological tissues to be extracted.

A greater understanding of the aforesaid embodiments and of many advantages thereof may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

The subject matter further includes, but not limited to, the following exemplified embodiments.

Embodiment 16. A method for ultrasound imaging, the method comprising:

transmitting an incident signal towards an object of interest;

receiving sets of the reflected signals from the object of interest; and decoding the reflected signals to recover an output, wherein the incident signal is an array comprised of sets of N number of titled cascaded waves and M number of sub-apertures, wherein $N=2^k$ and k is an integer, wherein $M=2^q$ and q is an integer, wherein the waves of the incident signal have predetermined polarities.

Embodiment 17. The method of embodiment 16, wherein each set of N waves contains at least two source signals.

Embodiment 18. The method of any one of embodiments 16-17, wherein the incident signal is expressed as follows:

$$X_C = \begin{bmatrix} X_1 \\ X_2 \\ \vdots \\ X_M \end{bmatrix} = \begin{bmatrix} x_{11}(t) & x_{12}(t) & \cdots & x_{1M}(t) \\ x_{21}(t) & x_{22}(t) & \cdots & x_{2M}(t) \\ \vdots & \vdots & \vdots & \vdots \\ x_{M1}(t) & x_{M2}(t) & \cdots & x_{MM}(t) \end{bmatrix}$$

where $X_1$, $X_2$, ..., $X_M$ represent transmitted signals for the $1^{th}$, $2^{rd}$, ..., $M^{th}$ transmission-reception events, and $x_{11}(t)$, $x_{1M}(t)$, ..., $x_{MM}(t)$ represent the transmitted signals from subarrays, the transmitted signals in the $m^{th}$ transmission and $n^{th}$ subarray are given by $$x_{mk}(t) = \Sigma_{i=1}^{N} c_{li} \cdot s_k(t) * \delta(t-(i-1) \cdot \tau),$$

where $s_n(t)$ is source signal of the $n^{th}$ subarray, $\tau$ is preset delay added between waves, $c_{li}$ is the coefficients of each cascaded wave.

Embodiment 19. The method of any one of embodiments 16-18, wherein the polarity coefficients of the waves from each sub-aperture are given by matrix $C_N H_M$ based on an M×M Hadamard matrix and Cascaded Dual-polarity Waves (CDW) matrix:

wherein the CDW matrix is generated by determining a number of waves, N, transmitted in the incident signal;

providing a 2×2 Hadamard matrix;

repeating the Hadamard matrix to obtain a 2×N first matrix;

providing a 2×N second matrix be taking each element in the 2×N first matrix to form a column vector and concatenating the N column vectors; and providing a third 2×N matrix by element wise multiplication of the 2×N first matrix and the 2×N second matrix.

Embodiment 20. The method of any one of embodiments 16-19, wherein an incident wave is diverging wave, and whether the diverging wave is tilted or not depends on information of tissue of a subject to be extracted.

Embodiment 21. The method of any one of embodiments 16-20, wherein the decoding the reflected signal comprises CDW decoding process and Hadamard decoding process.

Embodiment 22. The method of any one of embodiments 16-21, wherein the ultrasound imaging is 2D imaging or 3D imaging or 4D imaging.

Embodiment 23. A non-transitory computer readable storage medium comprising stored instruction thereon, the instructions when executed cause a processor to:

transmit an incident signal towards an object of interest;
receive sets of reflected signals from the object of interest; and
decode the reflected signals to recover an output,
wherein the incident signal is an array comprised of sets of N number of titled cascaded waves and M number of sub-apertures,
wherein $N=2^k$ and k is an integer,
wherein $M=2^q$ and q is an integer,
wherein the waves of the incident signal have predetermined polarities.

Embodiment 24. The non-transitory computer readable storage medium of embodiment 23, wherein the polarity coefficients of the waves from each sub-aperture are given by matrix $C_N H_M$ based on an M×M Hadamard matrix and Cascaded Dual-polarity Waves (CDW) matrix:

wherein the instructions when executed further cause a processor to generate the CDW matrix by determining a number of waves, N, transmitted in the incident signal;
providing a 2×2 Hadamard matrix;
repeating the Hadamard matrix to obtain a 2×N first matrix;
providing a 2×N second matrix be taking each element in the 2×N first matrix to form a column vector and concatenating the N column vectors; and
providing a third 2×N matrix by element wise multiplication of the 2×N first matrix and the 2×N second matrix.

Example 3

The proposed uCUS imaging sequence with CaSA was tested on a calibration phantom (CIRS) and in vivo human beating heart for B-mode imaging, myocardial motion, and blood flow imaging. The SA, H-SA, and CaSA imaging sequences were successively performed to ensure the same frame rate and same scanning region of interest for comparison. The data were acquired by a Verasonics Vantage 256 system (Verasonics, Kirkland, Wash.) with a phased array transducer P4-2 (64 array elements) whose center frequency was 2.5 MHz. The phased array was divided into four sub-apertures (M=4) with 16 elements each. The distance between the virtual source and the array is half of the sub-aperture. The number of cascaded waves is 32 (N=32) with 0.6 us short time interval for each two adjacent cascaded waves. The base of the transmitted diverging wave was a short burst of one cycle. The acquisition frame rate was 4000 frame per second (fps). The transmitted voltage for B-mode and Doppler images were 1.6V and 16.0 V, respectively.

The B-mode (brightness) images were obtained by the log compression of the envelope of the beamformed (pixel-oriented delay-and-sum) echoes. In the calibration phantom study, the quantitative evaluation metrics, such as resolution, SNR, and contrast, were computed from 100 acquired images at the same scanning region. In the in vivo beating human heart study, a human heart (male, 26 y.o.) was scanned in the apical four-chamber view. The electrocardiography (ECG) signals were also recorded to record the cardiac phase.

Figure 16:
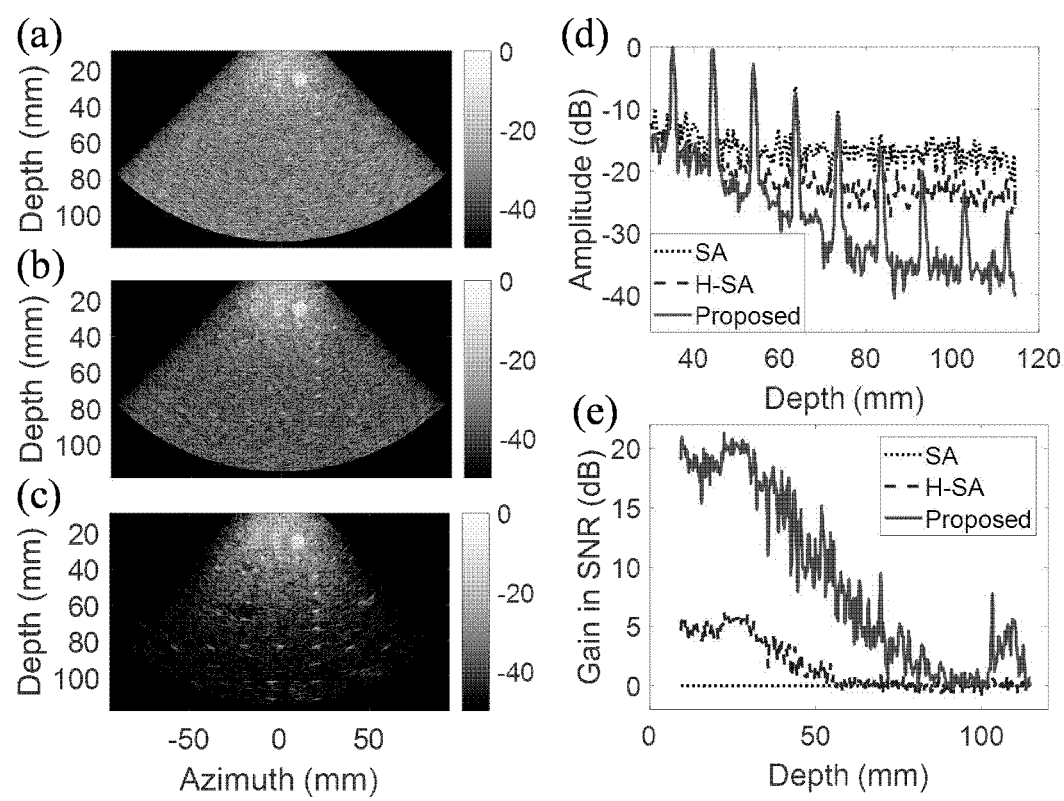
FIG. 16 (a) shows an example of B-mode image of a calibration phantom by SA method.

FIGS. 16(a)-(e) show the B-mode images, axial profiles, and SNR curves of the SA, H-SA, and proposed CaSA method realized in the phantom which contains multiple strong reflectors and hypoechoic cysts. In the SA image (FIG. 16(a)), the strong reflectors and hypoechoic cysts were veiled by the background noise, especially at the depth larger than 60 mm. In the H-SA image (FIG. 16(b)), the strong reflectors were revealed up to 80 mm deep and the hypoechoic cysts remained obscured. In contrast, the proposed CaSA method (FIG. 16(c)) was capable of highlighting the strong reflectors even in the deep zone and clearly displayed two cysts located at the depths of 40 mm and 63 mm at −17 mm azimuthally. Besides, the axial profiles around azimuth of 20 mm show significant suppression of the background noise by the proposed CaSA. FIG. 16(d) shows the axial profiles along the strong reflectors around azimuth 20 mm. FIG. 16(e) shows the gains in SNR of H-SA and CaSA with respect to SA were approximately 5 dB and and 20 dB, respectively.

TABLE II

COMPARISONS OF RESOLUTION, CONTRAST, SNR, AND FRAME RATE

| Symbol | SA | H-SA | CaSA | CaSA Vs. SA | CaSA Vs. H-SA |
|---|---|---|---|---|---|
| Axial resolution (mm) | 1.06 ± 0.081 | 1.05 ± 0.047 | 1.07 ± 0.006 | (−0.93%) | (−1.86%) |
| Lateral resolution (mm) | 1.52 ± 0.557 | 1.42 ± 0.033 | 1.43 ± 0.006 | (+6.29%) | (−0.70%) |
| CR (dB) | 0.70 ± 0.769 | 1.33 ± 0.790 | 9.14 ± 0.657 | (+8.44) | (+7.81) |
| CNR (dB) | 0.11 ± 0.119 | 0.20 ± 0.118 | 1.16 ± 0.068 | (+1.05) | (+0.96) |
| SNR (dB) | 20.26 | 25.89 | 40.72 | (+20.46) | (+14.83) |
| Frame rate (fps) | 1000 | 1000 | 1000 | (+0%) | (+0%) |

Table II showed the spatial (i.e., axial and lateral) resolutions, contrasts (CR and CNR), and SNR of the SA, H-SA and proposed CaSA imaging methods realized at the same frame rate. The spatial resolutions were calculated at the strong reflector at 0.8 mm azimuthally and depth of 34.5 mm. The proposed CaSA shows comparable spatial resolutions with SA and H-SA imaging. The CR and CNR were calculated at the cyst region around depth 63 mm. The H-SA method shows slight CR and CNR improvements by the SA method. The proposed CaSA method shows greater improvement of CR (+8.44 dB Vs. SA, +7.81 dB Vs. H-SA) and CNR (+1.05 Vs. SA, +0.96 Vs. H-SA). SNR calculated at the middle of the strong reflector region at depth of 26.18 mm by H-SA was improved by 5.63 dB from SA imaging. The proposed CaSA imaging shows the improvement of SNR (+20.46 dB Vs. SA, +14.83 dB Vs. H-SA).

Figure 17:
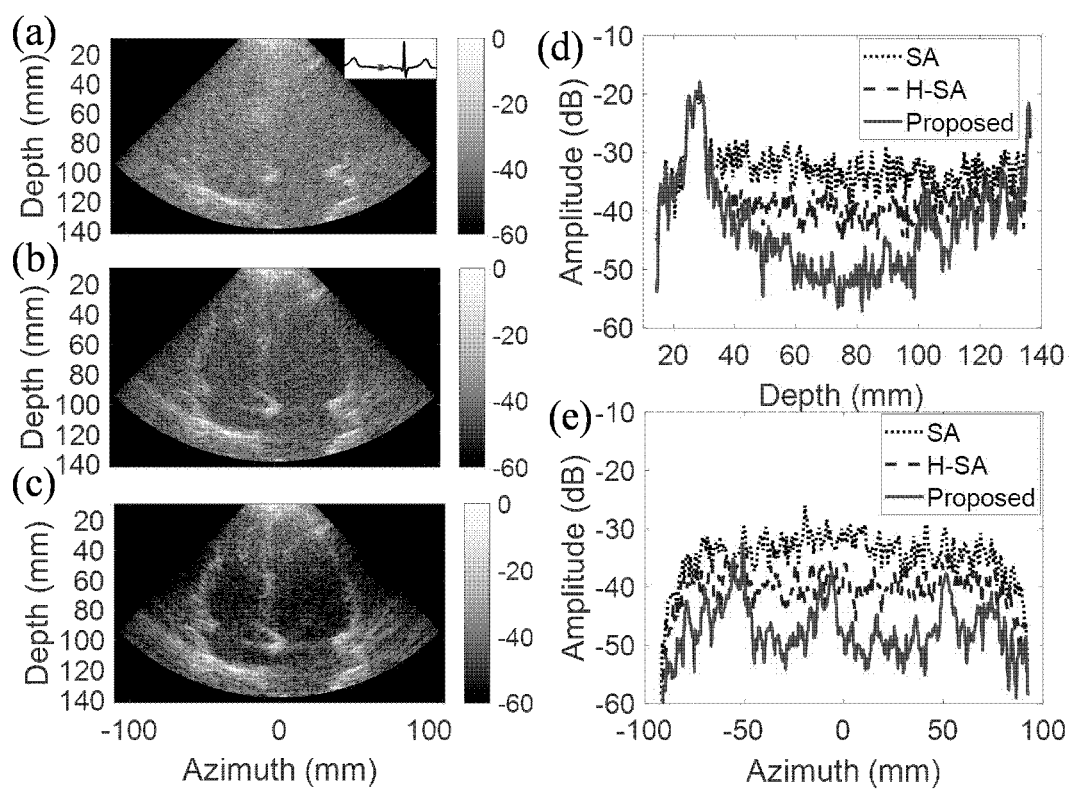
FIGS. 17 (a)-(c) show examples of B-mode images of an in vivo human heart in the apical four chamber view using SA, H-SA, and CaSA methods, respectively.
Figure 18:
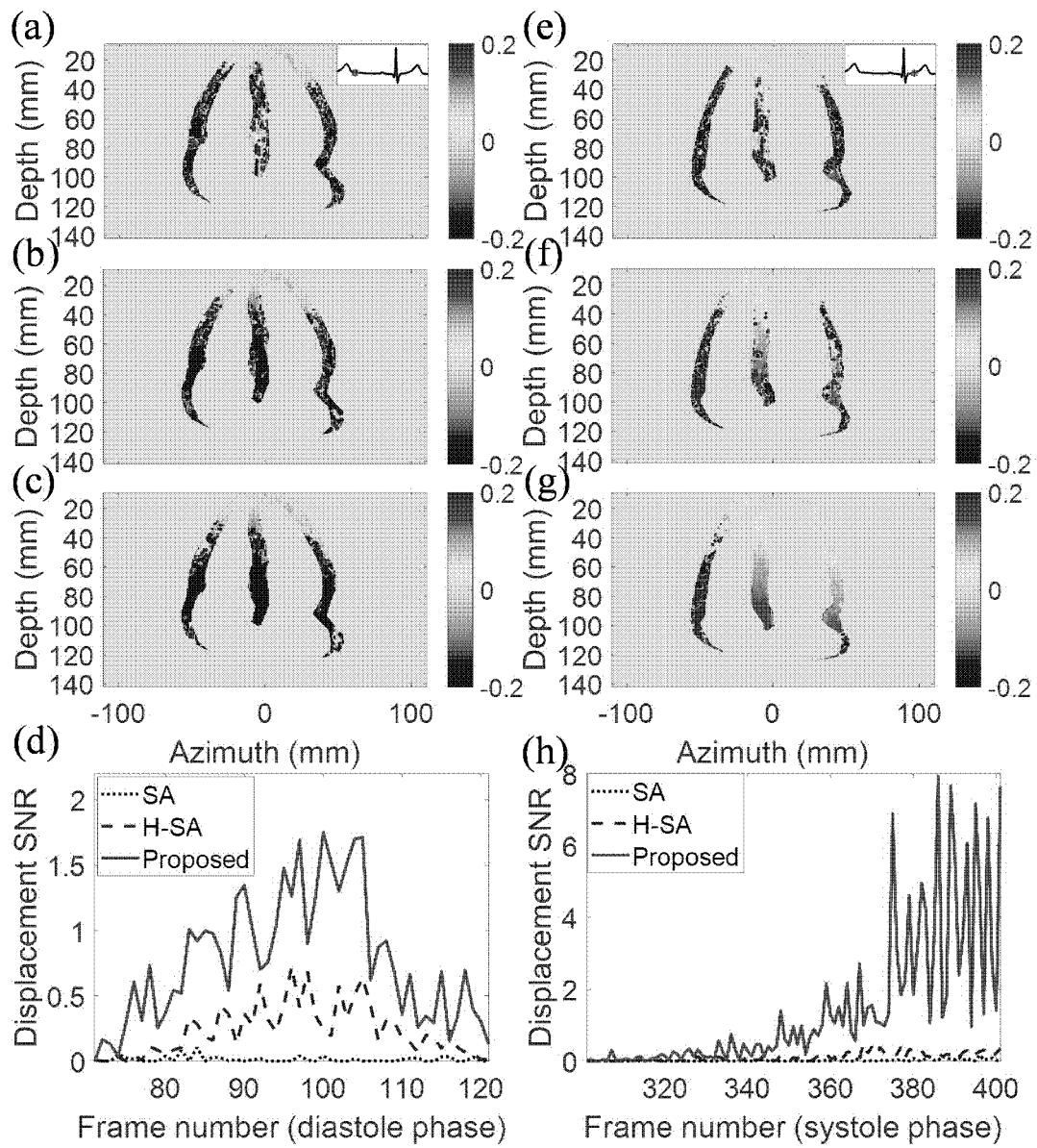
FIGS. 18 (a)-(c) show examples of the displacement maps of the myocardium in the apical four-chamber view based on respective SA, H-SA and CaSA reconstructed images at a diastolic phase.
Figure 19:
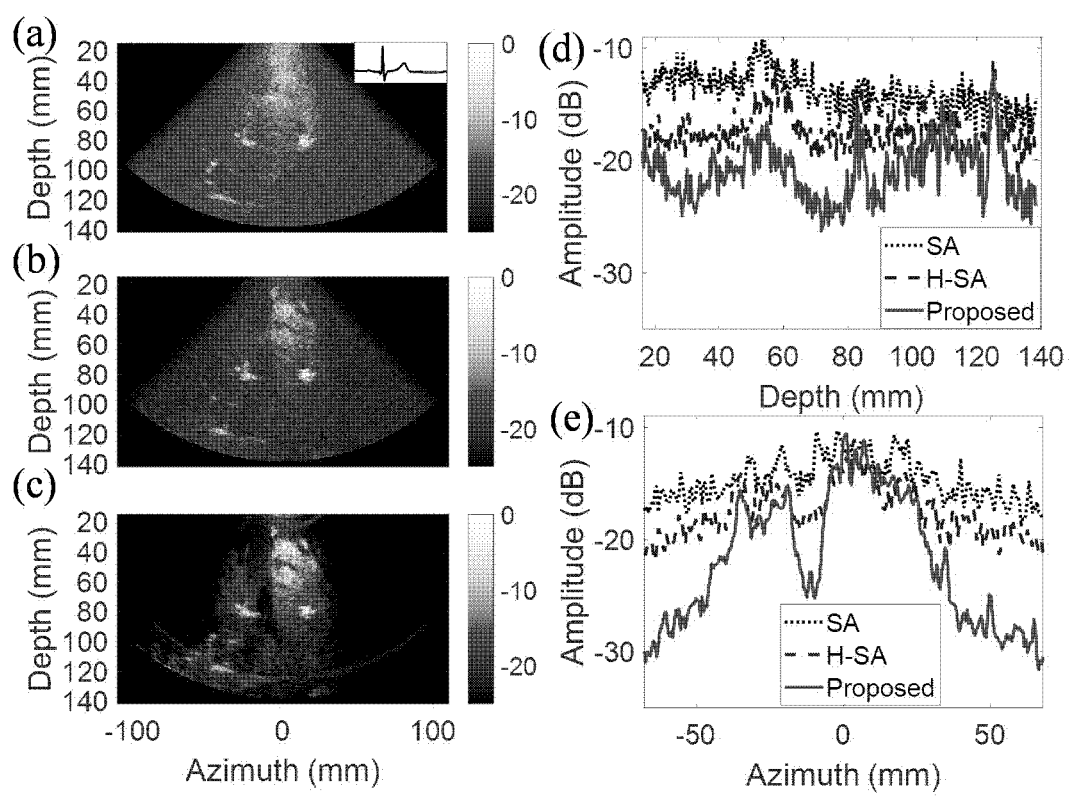
FIGS. 19 (a)-(c) show examples of the power Doppler images of the in vivo human heart during diastole by respective SA, H-SA, and CaSA method.

FIGS. 17(a)-(e) show the B-mode images of the in vivo human heart in the diastolic phase in the apical four-chamber view. The chamber walls were best visualized and delineated from the proposed CaSA method. FIGS. 17(a)-17(c) respectively shows the B-mode images of an in vivo human heart in the apical four-chamber view based on (a) SA, (b) H-SA, and (c) the proposed CaSA. The axial profile (FIG. 17(d)) was obtained at azimuth 29.2 mm through the left ventricle and left atrium. The lateral profile (FIG. 17(e)) was obtained at depth of 78.2 mm through both ventricles. The noise levels in the left ventricle at 78 mm in depth were approximately −35 dB for SA imaging, −40 dB for H-SA imaging, and −52 dB for CaSA imaging.

An in-house RF-based speckle tracking method based on cross-correlation with a 2D matching kernel was employed to estimate the axial displacement of the myocardium. Linear interpolation was first performed between RF signals in the post-displaced frame to increase lateral sampling. Two-dimensional cross-correlation was then performed between the pre-displaced and post-displaced RF frames in a predefined 2D search region to generate a normalized cross correlation (NCC) map, whose peak was used to derive the integer-sample displacement. An interpolation was further performed around this peak to refine the displacement to a subsample scale. In this example, only the axial displacement was estimated and presented to compare the estimation quality from RF frames reconstructed by SA, H-SA, and CaSA methods. Displacement SNR was calculated as the ratio of the squared displacement amplitude to the variance of the displacement amplitude within a region of interest (ROI) at each instant of interest within one cardiac cycle. In this example, the entire septum was chosen as the ROI to compare the estimation quality of the axial displacement among the three image reconstruction methods.

FIGS. 18(a)-(h) show the images of axial displacements estimated by the RF speckle tracking technique of the inventors from RF frames of the same human myocardium shown in FIGS. 17(a)-(e) reconstructed by SA, H-SA, and CaSA methods. Positive and negative axial displacements represent upward and downward myocardial motion, respectively. Superior quality of the axial displacements estimated from the proposed CaSA method was demonstrated in not only the temporal profile of displacement SNR during diastole (FIG. 18(d)) and systole (FIG. 18(h)) but also the spatial maps (FIGS. 18(c) and (g)) in comparison with SA (FIGS. 18(a) and (e)) and H-SA (FIGS. 18(b) and (f)).

In addition to the B-mode imaging, blood dynamics displayed as power Doppler images were obtained from the in vivo human beating heart. 70 post-compounded images were acquired to generate one power Doppler image. The tissue clutter filter is the similar to, in which a singular value decomposition (SVD) filter was applied for spatial-temporal processing of the blood and tissue information. The cutoff singular value was 60.

FIGS. 19(a)-(e) show the power Doppler images of the blood dynamics in the four-chamber view. According to the images (FIGS. 19(a)-(c)) and the axial profile (FIG. 7(d)) and lateral profile (FIG. 7(e)), the proposed CaSA imaging method shows the best contrast between the blood flow and the myocardial region.

Although some examples are given based on 2D imaging, the method of the present embodiments can also be used for 3D imaging or 4D imaging. 3D images in the present disclosure may refer to 3D images in spatial dimensionality or a time series of 2D images, and 4D images in the present disclosure may refer to a time series of 3D images.

Figure 20:
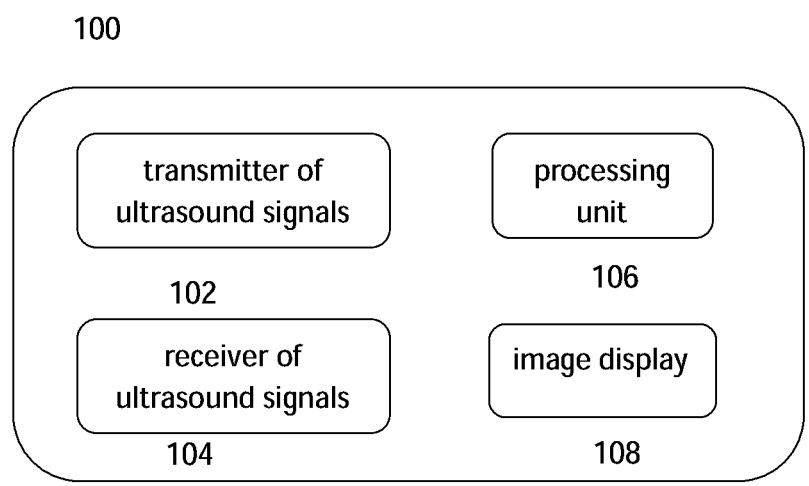
FIG. 20 is a block diagram of the ultrasound imaging system according to various embodiments.

FIG. 20 shows a block schematic diagram of the ultrasound imaging system. As shown in FIG. 20, the ultrasound imaging system 100 includes a transmitter of the ultrasound signals 102, a receiver of the ultrasound signals 104, a processing unit 106, and an image display 108, among others.

The transmitter 102 may transmit an incident signal towards the object of interest, and the receiver 104 may receive sets of the reflected signals from the object of interest. The transmitter may be typical and/or standard transmitter in the art, and also the receiver may be typical and/or standard receiver in the art. The processing unit 106 may perform the encoding and/or decoding process as described in the aforesaid embodiments. For instance, the processing unit 106 may perform the decoding process as shown in FIGS. 14 and 15. The image display 108 may output an image formed by the decoded signals. For instance, the image display 108 may display the images as shown in FIGS. 16-19.

The processing unit 106 may include software, hardware or some combination thereof. The software in the processing unit 12 may include instructions stored in a memory, such as the external memory or an internal memory of the processing unit. The processing unit 12 may include a processor, such as, a central processing unit (CPU), a graphics processing unit (GPU), Microprocessor (MPU) or the combination thereof.

Embodiment 25. An ultrasound imaging system, comprising:

a transmitter configured to transmit an incident signal towards an object of interest;

a receiver configured to receive sets of reflected signals from the object of interest; and a processor configured to decode the reflected signals to recover an output, wherein the incident signal is a pulse wave comprised of sets of N number of titled cascaded waves, wherein N=2k and k being a integer, wherein the waves of the incident signal have predetermined polarities, and wherein decoding comprises summing, subtracting, and delaying operations on the reflected or backscattered waves to obtain a processed signal.

Embodiment 26. The system according to embodiment 25, wherein a set of incident signal waves is expressed as follows:

$$\begin{cases} x_{s1}(t) = \sum_{i=1}^{2^{k-1}} a_{1i} \cdot s_1(t) * \delta(t - (i-1) \cdot \tau) + \\ \qquad \sum_{i=2^{k-1}+1}^{N} a_{1i} \cdot s_2(t) * \delta(t - (i-1) \cdot \tau) \\ x_{s2}(t) = \sum_{i=1}^{2^{k-1}} a_{2i} \cdot s_1(t) * \delta(t - (i-1) \cdot \tau) + \\ \qquad \sum_{i=2^{k-1}+1}^{N} a_{2i} \cdot s_2(t) * \delta(t - (i-1) \cdot \tau) \end{cases}$$

wherein each set of N waves contains two source signals, $s_1(t)$ and $s_2(t)$.

Embodiment 27. The system according to any of embodiments 25-26, wherein the polarities of the waves are determined as follows:

determining a number of waves, N, transmitted in the incident signal;

providing a 2×2 Hadamard matrix;

repeating the Hadamard matrix to obtain a 2×N first matrix;

providing a 2×N second matrix be taking each element in the 2×N first matrix to form a column vector and concatenating the N column vectors; and providing a 2×N third matrix by element wise multiplication of the 2×N first matrix and the 2×N second matrix.

Embodiment 28. The system according to any of embodiments 25-27, wherein an incident tilted wave is a plane wave, diverging wave, or a focused wave.

Embodiment 29. The system according to any of embodiments 25-28, wherein the object of interest is animal tissue.

Embodiment 30. The system according to any of embodiments 25-29, wherein the waves are emitted at a pulse repetition frequency below 20,000 Hz.

Embodiment 31. The system according to any of embodiments 25-30, wherein the waves are emitted at a pulse repetition frequency above 20,000 Hz.

Embodiment 32. An ultrasound imaging system, comprising:

a transmitter configured to transmit an incident signal towards an object of interest;

a receiver configured to receive sets of the reflected signals from the object of interest; and a processor configured to decode the reflected signals to recover an output, wherein the incident signal is an array comprised of sets of N number of titled cascaded waves and M number of sub-apertures, wherein $N=2^k$ and k is an integer, wherein $M=2^q$ and q is an integer, wherein the waves of the incident signal have predetermined polarities.

Embodiment 33. The system of embodiment 32, wherein each set of N waves contains at least two source signals.

Embodiment 34. The system of any one of embodiments 32-33, wherein the incident signal is expressed as follows:

$$X_C = \begin{bmatrix} X_1 \\ X_2 \\ \vdots \\ X_M \end{bmatrix} = \begin{bmatrix} x_{11}(t) & x_{12}(t) & \cdots & x_{1M}(t) \\ x_{21}(t) & x_{22}(t) & \cdots & x_{2M}(t) \\ \vdots & \vdots & \vdots & \vdots \\ x_{M1}(t) & x_{M2}(t) & \cdots & x_{MM}(t) \end{bmatrix}$$

where $X_1, X_2, \ldots, X_M$ represent transmitted signals for the $1^{th}, 2^{rd}, \ldots, M^{th}$ transmission-reception events, and $x_{11}(t), x_{1M}(t), \ldots, x_{MM}(t)$ represent the transmitted signals from subarrays, the transmitted signals in the $m^{th}$ transmission and $n^{th}$ subarray are given by $$x_{mn}(t) = \Sigma_{i=1}^N c_{li} \cdot s_n(t) * \delta(t-(i-1) \cdot \tau)$$

where $s_n(t)$ is source signal of the $n^{th}$ subarray, τ is preset delay added between waves, $c_{li}$ is the coefficients of each cascaded wave.

Embodiment 35. The system of any one of embodiments 32-34, wherein the polarity coefficients of the waves from each sub-aperture are given by matrix $C_N H_M$ based on an M×M Hadamard matrix and Cascaded Dual-polarity Waves (CDW) matrix:

wherein the CDW matrix is generated by determining a number of waves, N, transmitted in the incident signal;

providing a 2×2 Hadamard matrix;

repeating the Hadamard matrix to obtain a 2×N first matrix;

providing a 2×N second matrix be taking each element in the 2×N first matrix to form a column vector and concatenating the N column vectors; and providing a third 2×N matrix by element wise multiplication of the 2×N first matrix and the 2×N second matrix.

Embodiment 36. The system of any one of embodiments 32-35, wherein an incident wave is diverging wave, and whether the diverging wave is tilted or not depends on information of tissue of a subject to be extracted.

Embodiment 37. The system of any one of embodiments 32-36, wherein decoding the reflected signal comprises CDW decoding process and Hadamard decoding process.

Embodiment 38. The system of any one of embodiments 32-37, wherein the ultrasound imaging is 2D imaging or 3D imaging or 4D imaging.

Although the above examples as shown in FIGS. 8-11 and 16-19 are related to the medical imaging, the proposed method and system in the embodiments are not limited to the medical imaging, but may be used to monitor the structural health of an object, such as a metal. Furthermore, the imaging system and method in the aforesaid embodiments may be applied to other array imaging, e.g. radar imaging, microwave imaging, etc., without limited to the ultrasound imaging.

According to the aforesaid embodiments, imaging sequence CaSA with a newly designed spatiotemporal coding matrix for each segment of the cascaded-wave solves the tradeoff between the axial resolution and the length of transmitted pulses. The advantage of the CaSA method includes that it strives to approach the physical limits of SNR in ultrafast ultrasound imaging and shows enhanced quality for the imaging of heart dynamics than SA and H-SA imaging methods.

The tradeoff between the resolution and the length of transmitted waves is resolved by the newly designed spatiotemporal coding matrix $C_N H_M$. Based on the $C_N H_M$ matrix, both the spatial and temporal domains of the array aperture are utilized to achieve the maximal SNR available. In the spatial domain, M sub-aperture diverging waves coded with the spatial coefficients are transmitted simultaneously, and the received signals for each sub-aperture diverging wave can then be separated by the spatial decoding process, without lateral resolution degradation and cross-talks from each sub-aperture diverging wave. In the temporal domain, the N cascaded diverging waves are transmitted as the cascaded-wave ultrasound with the temporal coding coefficients from the $C_N H_M$ matrix, and the received signals from each wave are separated from the temporal decoding process, without sacrificing the axial resolution.

Furthermore, the CaSA method can be extended to any $N=2^k$, $M=2^m$. Most importantly, at the lowest available voltage that drives the array probe, CaSA can achieve acceptable SNR. Medical ultrasound imaging may exert adverse mechanical and/or thermal effects on the living organism if the mechanical index (MI), thermal index (TI), and acoustic intensity parameters exceed the upper limits set

What is claimed is:

1. A method implemented by an ultrasound imaging system for ultrasound imaging, the method comprising:

transmitting, by a transmitter of the ultrasound imaging system, an incident signal towards an object of interest;

receiving, by a receiver of the ultrasound imaging system, sets of reflected signals from the object of interest;

signal processing, by a processing unit of the ultrasound imaging system, the reflected signals to recover an output;

displaying, by an image display of the ultrasound imaging system, the recovered output;

wherein the incident signal is an array comprised of sets of N number of tilted cascaded waves in a temporal domain and M represents a number of sub-apertures in a spatial domain, wherein $N=2^k$ and k is an integer, wherein $M=2^q$ and q is an integer, wherein the tilted cascaded waves of the incident signal have predetermined polarities, and wherein the signal processing comprises spatiotemporal coding generating polarity coefficients of the tilted cascaded waves from each sub-aperture by matrix $C_N H_M$ based on an M×M Hadamard matrix and Cascaded Dual-polarity Waves (CDW) temporal coding matrix of Cascaded Dual-polarity Waves perform synthetic-transmit-aperture (ST A) imaging, and wherein the spatiotemporal coding generates an SNR increase of $10 \times \log_{10}(N \times M)$, wherein N is the number of tilted cascaded waves and where M is the number of sub-apertures, wherein the CDW matrix is generated by
  determining the number of tilted cascaded waves, N, transmitted in the incident signal;
  providing a 2×2 Hadamard matrix comprising $$H_{2\times 2} = \begin{bmatrix} a_{11} & a_{12} \\ a_{21} & a_{22} \end{bmatrix};$$

repeating and rearranging each element of the 2×2 Hadamard matrix in a predetermined manner to obtain a 2×N first matrix, including steps of obtaining a 2×4 CDW matrix comprising $C_{2\times 4}$, wherein a first column is a column vector of $$a_{11} \cdot \begin{bmatrix} 1 \\ 1 \end{bmatrix},$$

a second column is a column vector of $$a_{21} \cdot \begin{bmatrix} 1 \\ -1 \end{bmatrix},$$

a third column is a column vector of $$a_{12} \cdot \begin{bmatrix} 1 \\ 1 \end{bmatrix},$$

a first column is a column vector of $$a_{22} \cdot \begin{bmatrix} 1 \\ -1 \end{bmatrix},$$

wherein · denotes scalar multiplication, then converting the $C_{2\times 4}$ matrix to a 2×8 CDW by partitioning the $C_{2\times 4}$ into four groups as $$\begin{bmatrix} A & B \\ C & D \end{bmatrix};$$

where A, B, C, and D, each is 1×2 row vector, then, obtaining the first and the second columns of the 2×8 CDW matrix by multiplication of $$\begin{bmatrix} 1 \\ 1 \end{bmatrix}$$

by the vector A, obtaining the third and the fourth columns of the 2×8 CDW matrix by multiplication of $$\begin{bmatrix} 1 \\ -1 \end{bmatrix}$$

by the vector C, obtaining the fifth and the sixth columns of the 2×8 CDW matrix by multiplication of $$\begin{bmatrix} 1 \\ 1 \end{bmatrix}$$

by the vector B, obtaining the seventh and the eighth columns of the 2×8 CDW matrix by multiplication of $$\begin{bmatrix} 1 \\ -1 \end{bmatrix}$$

by the vector D to generate the 2×8 CDQ matrix comprising $$\begin{bmatrix} A & C & B & D \\ A & -C & B & -D \end{bmatrix};$$

providing a 2×N second matrix by taking each element in the 2×N first matrix to form a column vector and concatenating N column vectors formed; and providing a third 2×N matrix by element wise multiplication of the 2×N first matrix and the 2×N second matrix.

2. The method of claim 1, wherein each set of N waves contains at least two source signals.

3. The method of claim 2, wherein the signal processing the reflected signals comprises Cascaded Dual-polarity Waves (CDW) signal processing and Hadamard processing.

4. The method of claim 2, wherein the ultrasound imaging is 2D imaging or 3D imaging or 4D imaging.

5. The method of claim 1, wherein the incident signal is expressed as follows:

$$X_C = \begin{bmatrix} X_1 \\ X_2 \\ \vdots \\ X_M \end{bmatrix} = \begin{bmatrix} x_{11}(t) & x_{12}(t) & \cdots & x_{1M}(t) \\ x_{21}(t) & x_{22}(t) & \cdots & x_{2M}(t) \\ \vdots & \vdots & \vdots & \vdots \\ x_{M1}(t) & x_{M2}(t) & \cdots & x_{MM}(t) \end{bmatrix}$$

where $X_1, X_2, \ldots, X_M$ represent transmitted signals for the $1^{st}, 2^{nd}, \ldots, M^{th}$ sub-aperture, and $x_{11}(t), x_{1M}(t), \ldots, x_{MM}(t)$ represent the transmitted signals from sub-apertures, while the transmitted signals in $m^{th}$ transmission and a $n^{th}$ sub-aperture are given by, $$x_{mn}(t) = \Sigma_{i=1}^{N} c_{li} s_n(t) * \delta(t-(i-1)\cdot\tau)$$

where $s_n(t)$ is source signal of a $n^{th}$ subarray, $\tau$ is preset delay added between waves, $c_{li}$ is coefficients of each cascaded wave wherein symbol l in coefficient $C_{li}$ represents a transmission number, and $\delta$ is a delta function, and wherein m is an integer greater than or equal to 2 and n is an integer greater than or equal to 1 and smaller than or equal to M.

6. A non-transitory computer readable storage medium comprising stored instructions thereon, the instructions when executed cause a processor to:

transmit, by a transmitter of an ultrasound imaging system, an incident signal towards an object of interest;

receive, by a receiver of the ultrasound imaging system, sets of reflected signals from the object of interest; and signal process, by a processing unit of the ultrasound imaging system, the reflected signals to recover an output; and display, by an image display of the ultrasound imaging system, the recovered output;

wherein the incident signal is an array comprised of sets of N number of tilted cascaded waves in a temporal domain and M number of sub-apertures in a spatial domain, wherein $N=2^k$ and k is an integer, wherein $M=2^q$ and q is an integer, wherein the tilted cascaded waves of the incident signal have predetermined polarities, and wherein the signal processing comprises spatiotemporal coding generating polarity coefficients of the waves from each sub-aperture by matrix $C_N H_M$ based on an M×M Hadamard matrix and a Cascaded Dual-polarity Waves (CDW) temporal coding matrix of Cascaded Dual-polarity Waves perform synthetic-transmit-aperture (STA) imaging, and wherein the spatiotemporal coding is configured to achieve generates an SNR increase of $10\times\log_{10}(N\times M)$, wherein N is the of number tilted cascaded waves and where M is the number of sub-apertures, wherein the CDW matrix is generated by determining the number of tilted cascaded waves, N, transmitted in the incident signal;

providing a 2×2 Hadamard matrix comprising $$H_{2\times2} = \begin{bmatrix} a_{11} & a_{12} \\ a_{21} & a_{22} \end{bmatrix};$$

repeating and rearranging each element of the 2×2 Hadamard matrix in a predetermined manner to obtain a 2×N first matrix, including steps of obtaining a 2×4 CDW matrix comprising $C_{2\times4}$, wherein a first column is a column vector of $$a_{11} \cdot \begin{bmatrix} 1 \\ 1 \end{bmatrix},$$

a second column is a column vector of $$a_{21} \cdot \begin{bmatrix} 1 \\ -1 \end{bmatrix},$$

a third column is a column vector of $$a_{12} \cdot \begin{bmatrix} 1 \\ 1 \end{bmatrix},$$

a first column is a column vector of $$a_{22} \cdot \begin{bmatrix} 1 \\ -1 \end{bmatrix},$$

wherein · denotes scalar multiplication, then converting the $C_{2\times4}$ matrix to a 2×8 CDW by partitioning the $C_{2\times4}$ into four groups as $$\begin{bmatrix} A & B \\ B & D \end{bmatrix};$$

where A, B, C, and D, each is 1×2 row vector, then, obtaining the first and the second columns of the 2×8 CDW matrix by multiplication of $$\begin{bmatrix} 1 \\ 1 \end{bmatrix}$$

by the vector A, obtaining the third and the fourth columns of the 2×8 CDW matrix by multiplication of $$\begin{bmatrix} 1 \\ -1 \end{bmatrix}$$

by the vector C, obtaining the fifth and the sixth columns of the 2×8 CDW matrix by multiplication of $$\begin{bmatrix} 1 \\ 1 \end{bmatrix}$$

by the vector B, obtaining the seventh and the eighth columns of the 2×8 CDW matrix by multiplication of $$\begin{bmatrix} 1 \\ -1 \end{bmatrix}$$

by the vector D to generate the 2×8 CDQ matrix comprising $$\begin{bmatrix} A & C & B & D \\ A & -C & B & -D \end{bmatrix};$$

providing a 2×N second matrix by taking each element in the 2×N first matrix to form a column vector and concatenating N column vectors formed; and providing a third 2×N matrix by element wise multiplication of the 2×N first matrix and the 2×N second matrix.

7. The non-transitory computer readable storage medium of claim 6:
wherein the instructions when executed further cause a processor to generate the CDW matrix by
determining the number of tilted cascaded waves, N, transmitted in the incident signal;
providing a 2×2 Hadamard matrix;
repeating and rearranging each element of the 2×2 Hadamard matrix in a predetermined manner to obtain a 2×NV first matrix;
providing a 2×N second matrix be taking each element in the 2×N first matrix to form a column vector and concatenating N column vectors formed; and
providing a third 2×N matrix by element wise multiplication of the 2×N first matrix and the 2×N second matrix.

8. The non-transitory computer readable storage medium of claim 6, wherein the object of interest is tissue of a subject.

9. The non-transitory computer readable storage medium of claim 6, wherein the signal processing the reflected signals comprises Cascaded Dual-polarity Waves (CDW) signal processing and Hadamard signal processing.

\* \* \* \* \*

UNITED STATES PATENT AND TRADEMARK OFFICE
CERTIFICATE OF CORRECTION

PATENT NO. : 11,852,754 B2  
APPLICATION NO. : 16/767009  
DATED : December 26, 2023  
INVENTOR(S) : Yang Zhang, Yuexin Guo and Wei-Ning Lee Page 1 of 2

It is certified that error appears in the above-identified patent and that said Letters Patent is hereby corrected as shown below:

In the Claims

<u>Column 27,</u>
Line 25, Claim 1, "output;" should read --output; and--.
Lines 40-41, Claim 1, "matrix and Cascaded" should read --matrix and a Cascaded--.
Line 43, Claim 1, "(ST A)" should read --(STA)--.
Lines 46-47, Claim 1, "sub-apertures," should read --sub-apertures;--.

<u>Column 28,</u>
Lines 10-14, Claim 1, "$a_{12} \cdot \begin{bmatrix}1\\1\end{bmatrix}$, a first column" should read --$a_{12} \cdot \begin{bmatrix}1\\1\end{bmatrix}$, a fourth column--.
Lines 10-14, Claim 1, "CDW by" should read --CDW matrix by--.
Lines 25-28, Claim 1, "$\begin{bmatrix}A & B\\C & D\end{bmatrix}$, where A, B, C, and D, each" should read --$\begin{bmatrix}A & B\\C & D\end{bmatrix}$, where A, B, C, and D each--.
Line 59, Claim 1, "CDQ" should read --CDW--.

<u>Column 29,</u>
Line 28, Claim 5, "$x_{mn}(t)=\Sigma_{i=1}^{N}c_{li}s_n(t)*\delta(t-(i-1)\cdot\tau)$" should read
--$x_{mn}(t) = \sum_{i=1}^{N} c_{li} s_n(t) * \delta(t - (i - 1) \cdot \tau)$--.
Line 43, Claim 6, "interest; and" should read --interest;--.
Line 58, Claim 6, "the waves" should read --the tilted cascaded waves--.
Line 62, Claim 6, "Waves perform" should read --Waves configured to perform--.
Line 63, Claim 6, "(ST A) imaging, and" should read --(STA) imaging and non-synthetic-transmit-aperture imaging, and--.
Line 64, Claim 6, "configured to achieve generates an SNR" should read --configured to achieve an SNR--.
Lines 65-66, Claim 6, "wherein $N$ is the of number tilted" should read --where $N$ is a number of Signed and Sealed this  
Twenty-third Day of April, 2024

Katherine Kelly Vidal  
*Director of the United States Patent and Trademark Office*

CERTIFICATE OF CORRECTION (continued)
U.S. Pat. No. 11,852,754 B2 tilted--.
Lines 66-67, Claim 6, "M is the number of sub-apertures," should read --M is a number of sub-apertures;--.

Column 30,

Lines 31-35, Claim 6, "$a_{12} \cdot \begin{bmatrix} 1 \\ 1 \end{bmatrix}$, a first column" should read --$a_{12} \cdot \begin{bmatrix} 1 \\ 1 \end{bmatrix}$, a fourth column--.

Line 47, Claim 6, "$\begin{bmatrix} A & B \\ B & D \end{bmatrix}$;" should read --$\begin{bmatrix} A & B \\ C & D \end{bmatrix}$;--.

Line 50, Claim 6, "D, each" should read --D each--.

Column 31,
Line 13, Claim 6, "CDQ" should read --CDW--.

Column 32,
Line 10, Claim 7, "2×NV" should read --2×N--.